US012624343B2

(12) United States Patent
Jurga

(10) Patent No.: US 12,624,343 B2
(45) Date of Patent: May 12, 2026

(54) EXTRACELLULAR VESICLES (EVs) DERIVED FROM MESENCHYMAL STROMAL CELLS AND METHOD FOR OBTAINING SAID EVs

(71) Applicant: EXO BIOLOGICS SA, Liege (BE)

(72) Inventor: Marcin Jurga, Liege (BE)

(73) Assignee: EXO BIOLOGICS SA, Liege (BE)

( * ) Notice: Subject to any disclaimer, the term of this patent is extended or adjusted under 35 U.S.C. 154(b) by 561 days.

(21) Appl. No.: 18/014,224

(22) PCT Filed: Jul. 8, 2021

(86) PCT No.: PCT/EP2021/068989
§ 371 (c)(1),
(2) Date: Jan. 3, 2023

(87) PCT Pub. No.: WO2022/008652
PCT Pub. Date: Jan. 13, 2022

(65) Prior Publication Data
US 2023/0257712 A1 Aug. 17, 2023

(30) Foreign Application Priority Data
Jul. 9, 2020 (EP) .................................... 20184893

(51) Int. Cl.
*C12N 5/0775* (2010.01)
*A61K 35/28* (2015.01)
*A61P 11/00* (2006.01)

(52) U.S. Cl.
CPC ............ *C12N 5/0665* (2013.01); *A61K 35/28* (2013.01); *A61P 11/00* (2018.01)

(58) Field of Classification Search
None
See application file for complete search history.

(56) References Cited

U.S. PATENT DOCUMENTS

| | | | | |
|---|---|---|---|---|
| 11,993,787 | B2 * | 5/2024 | Stice ........................ | A61P 25/02 |
| 12,139,723 | B2 * | 11/2024 | Stice ........................ | A61P 25/16 |
| 2017/0121685 | A1 | 5/2017 | De La Rosa et al. | |
| 2019/0060368 | A1 * | 2/2019 | Lee ........................ | A61K 35/28 |

FOREIGN PATENT DOCUMENTS

| | | |
|---|---|---|
| CN | 102827807 A | 12/2012 |
| JP | H11506610 A | 6/1999 |
| JP | 2018531979 A | 11/2018 |
| WO | 9639487 A1 | 12/1996 |
| WO | 2013084001 A1 | 6/2013 |
| WO | 2017076924 A1 | 5/2017 |

OTHER PUBLICATIONS

WIPO, ISR for PCT/EP2021/068989, Oct. 11, 2021.
Haraszti et al., Exosomes Produced from 3D Cultures of MSCs by Tangential Flow Filtration Show Higher Yield and Improved Activity, Molecular Therapy, Dec. 2018, 2838-2847, vol. 26, No. 12.
Hoang et al., Differential Wound Healing Capacity of Mesenchymal Stem Cell-Derived Exosomes Originated from Bone Marrow, Adipose Tissue and Umbilical Cord Under Serum—and Xeno-Free Condition, Frontiers in Molecular Biosciences, Jun. 2020, 1-13, vol. 7, Article 119.
Chase et al., Development and Characterization of a Clinically Compliant Xeno-Free Culture Medium in Good Manufacturing Practice for Human Multipotent Mesenchymal Stem Cells, Stem Cells Translational Medicine, 2012, 750-758, vol. 1.
Monsel et al., Mesechymal Stem Cell Derived Secretome and Extracellular Vesicles for Acute Lung Injury and Other Inflammatory Lung Diseases, Expert Opinion on Biological Therapy, 2016, 859-871, vol. 16(7).
Park et al., Metabolic Effects of Albumin Therapy in Acute Lung Injury Measured by 1H-NMR Spectroscopy of Plasma: A Pilot Study, Critical Care Medicine, Oct. 2011, 2308-2313, vol. 39(10).
Sengupta et al., "Exosomes Derived from Bone Marrow Mesenchymal Stem Cells as Treatment for Severe COVID-19," Stem Cells and Development, 2020, vol. 29, No. 12, pp. 747-754.
Bian et al., "Extracellular vesicles derived from human bone marrow mesenchymal stem cells promote angiogenesis in a rat myocardial infarction model," J Mol Med, 2014, vol. 92, pp. 387-397.
Balaj et al., "Heparin affinity purification of extracellular vesicles," Scientific Reports, May 19, 2015, vol. 5.
Momen-Heravi et al., "Exosome-mediated delivery of functionally active miRNA-155 inhibitor to macrophages," Nanomedicine, Oct. 2014, vol. 10, No. 7, pp. 1517-1527.
CNIPA, Office Action issued for CN Patent Application No. 202180047382.1, Sep. 30, 2025.

* cited by examiner

*Primary Examiner* — Blaine Lankford
(74) *Attorney, Agent, or Firm* — Hodgson Russ LLP

(57) ABSTRACT

The current invention relates to a process for the manufacturing of a composition of extracellular vesicles (EVs) derived from mesenchymal stromal cells (MSCs), said method comprises: culturing and expanding MSCs in a serum-free and xeno-free medium comprising purified human serum albumin and human transferrin; —collecting cell supernatant, said cell supernatant comprises EVs; —filtering said cell supernatant to obtain EVs; and concentrating said EVs, preferably by means of ultrafiltration. In a second and further aspect, said invention is directed to compositions comprising EVs and their clinical use.

12 Claims, 1 Drawing Sheet

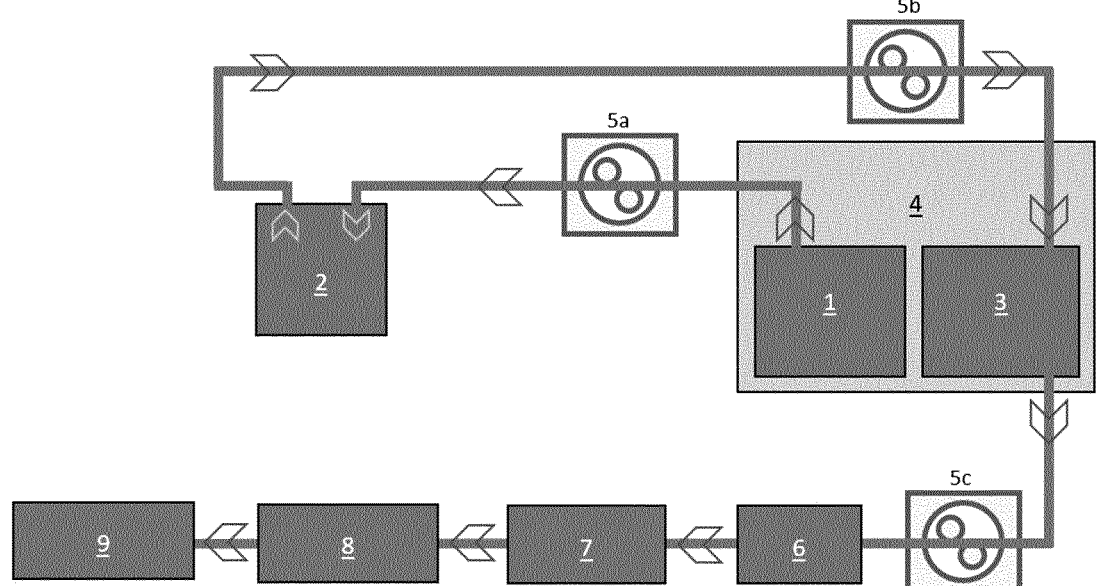

1

EXTRACELLULAR VESICLES (EVs) DERIVED FROM MESENCHYMAL STROMAL CELLS AND METHOD FOR OBTAINING SAID EVs

FIELD OF THE INVENTION

The present invention relates to extracellular vesicles (EVs) derived from mesenchymal stromal cells (MSCs) and compositions comprising said vesicles as well as methods for obtaining the latter.

BACKGROUND

EVs are lipid bilayer-delimited particles that are naturally released from a cell and, unlike a cell, cannot replicate. EVs range in diameter from near the size of the smallest physically possible unilamellar liposome (around 20-30 nanometers) to as large as 10 microns or more, although the vast majority of EVs are smaller than 200 nm. They carry a cargo of proteins, nucleic acids, lipids, metabolites, and even organelles from the parent cell. Most cells that have been studied to date are thought to release EVs, including some bacterial, fungal, and plant cells that are surrounded by cell walls. A wide variety of EV subtypes have been proposed, defined variously by size, biogenesis pathway, cargo, cellular source, and function, leading to a historically heterogenous nomenclature including terms like exosomes, microvesicles and ectosomes.

EVs could be used for therapeutic purposes, such as delivering nucleic acids or other cargos to diseased tissue and cells. This growing interest was paralleled by formation of companies and funding programs focused on development of EVs as biomarkers or therapies of disease, the founding of an International Society for Extracellular Vesicles (ISEV), and establishment of a scientific journal devoted to the field, the Journal of Extracellular Vesicles.

With the growing interest in EVs for therapeutic use, also the need for clinical-grade EVs has risen. In order to be useful in the clinic, EVs need to be produced in a reproducible and controlled manner. Good Manufacturing Practice (GMP) for the manufacturing of compositions comprising EVs is crucial, in order to assure that various batches produced are uniform and of consistent quality. GMP is particularly difficult when dealing with cell-derived therapeutics.

Production processes for exosomes derived from mesenchymal stromal cells (MSCs) are known from, for example, Reka Agnes Haraszti et al., 2018. In addition, Diem Huong Huang at al., 2020, describes MSC-derived exosomes in the context of their regenerative potential for cutaneous tissue, the exosomes produced under specific conditions. Various media may be used to culture MSCs, amongst which a serum-free and xeno-free culture medium as disclosed in Lucas G. Chase et al., 2012. Antoine Monsel et al., 2016, further, describe the use of MSC secretome and extracellular vesicles (EVs) in the treatment of lung diseases. The presented data for their use in humans is mostly speculative and highlight several problems in the state of the art, such as low reproducibility and low yield. In addition, the document warns about potential problems with the use of bioreactors for large scale culture of MSCs for the production of EVs. Finally, Youngja Park et al., 2011, refer to the use of albumin in the treatment of lung diseases.

Several problems, however, still need to be solved before the clinical use of EVs can become widespread. It remains a challenge to develop platforms for the production, storage and handling of clinical grade EVs in a reliable and reproducibly quantifiable manner. MSC-derived EV-based pharmaceuticals and subsequent clinical trials demand the resolution of several scientific, regulatory, technological and mechanistic issues prior to bringing MSC-derived EV-based therapies to the clinic.

There is thus need for a protocol that enables the production of clinical-grade MSC-derived EVs in a stable and reproducible manner, under GMP conditions, and at cost effective large scale. Moreover, there is a need for an EV-based product that has good stability and commercially attractive shelf life.

SUMMARY OF THE INVENTION

The current invention provides a method that enables the production of EVs from MSCs in a stable and repeatable manner, under GMP conditions according to the Internal Conference on Harmonization (ICH) 2020 GMP quality guidelines. The EV composition obtained is a clinical-grade, cGMP product that is readily useable in clinical trials and in patients and has good stability.

To that purpose, the current invention provides a manufacturing process and a composition. Preferred embodiments are described herein.

Said product may have various clinical applications and therapeutic effects. Uses of said product are described herein. Due to the long-term stability of said composition, the product can be used in various clinical applications.

DESCRIPTION OF FIGURES

FIG. 1 shows an embodiment of a MSC expansion unit and EV processing unit that can be used to produce EVs of the current invention.

DEFINITIONS

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight", "weight percent", "% wt" or "wt %", here and throughout the description unless otherwise defined, refers to the relative weight of the respective component based on the overall weight of the formulation.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

For the purpose of the current invention, the term "extracellular vesicles" or "EVs" is to be understood as micro or nano-meter sized particles secreted by different types of cells in vivo and in vitro including proteins associated with said EVs. EVs comprise proteins, growth factors, miRNA and other molecules encapsulated in a lipid sphere. EVs can be classified according to their size and intracellular origin. Exosomes are a subgroup of EVs that are typically in a size range of 0.1 micron or smaller. Exosomes are derived from multivesicular bodies, a late endosomal compartment, which are secreted via the fusion of multivesicular bodies with the plasma membrane. Another type of EV is the shedding vesicles (also known as microvesicles) which are a heterogenous population of membrane vesicles up to 1 micron in size directly released from the cell membrane through the disruption of the cortical cytoskeleton. All types of vesicles secreted by cells are defined in general as EVs.

The term "associated with EV(s)" in relation to substances means that said substance is either a) attached or bound to the surface layer of the EVs (by any type of binding, such as covalent or non-covalent binding) preferably by means of a non-covalent bond; and/or b) attached or bound within the surface layer of said EVs; and/or c) is internalized within said EVs.

Said substances associated with EVs may be any type of substances, such as, but not limited to molecules including amino acids, proteins, peptides, nucleic acids such as RNA and DNA (e.g. noncoding RNA, miRNA, mRNA), sugars, carbohydrates, fats, vitamins, growth factors, pro-angiogenic molecules, cardioprotective enzymes, antibodies, anti-inflammatory molecules, anti-fibrotic molecules, anti-oxidative molecules, pro-neurogenic molecules and anti-viral molecules; and ions such as metal ions or calcium ions.

The term "cell medium" or "cell culture medium" or "medium" refers to an aqueous solution of nutrients and other components of defined composition, which can be used for maintenance or growth of cells.

The term "serum-free" cell culture medium refers to a cell culture medium that does not contain animal or human serum, plasma or hemolymph. Said serum-free medium may contain ingredients that are processed or derived from blood, serum or plasma such as albumin, transferrin, low-density lipid and hormones. It may also contain other biological ingredients, preferably of known and fully reproducible composition and concentration, that are not serum, plasma or hemolymph (e.g., growth factors, hormones and carrier proteins).

The term "xeno-free" cell culture medium is to be understood as cell media that does not contain any components that are directly derived from non-human animals, or recombinant components manufactured from non-human animal DNA sequences.

The term "pharmaceutically acceptable carrier" as used herein, refers to a carrier or a diluent that does not cause significant irritation to a subject and does not abrogate the biological activity and properties of the administered composition. As an example, the pharmaceutically acceptable carrier may act as a stabilizer and/or as an adjuvant. Examples, without limitations, of carriers are propylene glycol, saline, emulsions and mixtures of organic solvents with water.

The term "sufficient amount" means an amount sufficient to produce a desired and measurable effect, e.g., an amount sufficient to alter a protein expression profile.

The term "therapeutically effective amount" is an amount that is effective to ameliorate a symptom of a disease. A therapeutically effective amount can be a "prophylactically effective amount" as prophylaxis can be considered therapy.

The term "treatment" refers to both therapeutic treatment and prophylactic or preventative measures, wherein the objective is to prevent or slow down (lessen) the targeted pathologic condition or disorder. Those in need of treatment include those already with the disorder as well as those prone to have the disorder or those in whom the disorder is to be prevented.

The term "composition" refers to compositions at any stage of the manufacturing process, including the final pharmaceutically acceptable product and any in-process intermediates thereof.

The term "treating" refers to reversing, preventing, alleviating or inhibiting the progress of a disease, disorder or condition, or one or more symptoms of a disease, disorder or condition. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms of a disease, disorder or condition. As used herein, "treating" may also refer to reducing the severity of a disease, disorder or condition or symptoms of such disease, disorder or condition prior to affliction with the disease, disorder or condition. Such prevention or reduction of the severity of a disease, disorder or condition prior to affliction relates to the administration of the composition of the present technology, as described herein, to a subject that is not at the time of administration afflicted with the disease, disorder or condition. As used herein "treating" may also further refer to preventing the recurrence of a disease, disorder or condition or of one or more symptoms of such disease, disorder or condition. The terms "therapy," "treatment," and "therapeutically," as used herein, refer to the act of treating as defined above.

The term "fibrosis" as used herein refers to the formation of excess fibrous connective tissue in an organ or tissue in a reparative or reactive process.

For the purpose of the current invention, the term "mesenchymal stromal cells" or "MSCs" is to be understood as stromal adherent cells able to differentiate into various cell types. Sources of MSCs are bone marrow, cord cells, adipose tissue, amniotic fluid, mammary glands, blood.

DETAILED DESCRIPTION OF THE INVENTION

The present invention concerns a method for the production of EVs from MSCs, the composition obtained by said method and its therapeutic use.

In a first aspect, the current invention is directed to a process for the manufacturing of a composition of EVs derived from MSCs. More in particular, said process comprises the following steps:

culturing and expanding MSCs in a serum-free and xeno-free medium comprising purified human serum albumin and human transferrin;

collecting cell supernatant, said cell supernatant comprises EVs;

filtering said cell supernatant to obtain EVs; and concentrating said EVs, preferably by means of ultrafiltration.

MSCs will be cultured and expanded in a vessel, preferably a bioreactor, more preferably a stirred-type tank bioreactor, for the use of the production of EVs. To that purpose, MSCs will be allowed to grow and expand in a culture medium that is serum- and xeno-free, supplemented with human serum albumin and transferrin. By making use of serum- and xeno-free growth medium for culturing and expanding said MSCs, the presence of unwanted contaminants in the EVs is avoided. Such contaminants may interfere with the further clinical use of the resulting EV product. Serum and platelet lysate generally comprises albumin and cell growth is often influenced by the level of albumin in the medium. The levels of albumin as for any other ingredient in serum and platelet lysate is however variable. In order to obtain clinical-grade EVs, the use of serum and/or platelet lysate is to be avoided.

Albumin is however a crucial component of the end-product as it aids in the stability and functionality of said EVs. "Stability" of a product, such as EVs, in present context refers to the capability of a particular formulation or product in a specific environment, such as a container or closed system, to remain within a predefined range of values of parameters of physical, chemical, microbiological, toxicological and functional specifications or characteristics, for a given period of time. Non-limiting examples of such parameters are particle number, particle size, leakage of internal components and activity.

As it aids in the stability of EVs, exogenous albumin should be present in said cell medium. In an embodiment, said medium therefore comprises human albumin, either recombinant or purified albumin, e.g. purified from human plasma. In a further embodiment, said albumin is present in said medium at a concentration of between 1 g/l and 5 g/l. The latter concentration was shown to be particularly useful in obtaining a good and stable end product.

The cell growth medium further comprises transferrin, preferably recombinant or purified transferrin, e.g. purified from plasma. Transferrins make up an extensive micro-heterogeneous group of single chain glycoprotein isotypes with approximate molecular weights of 78 to 80 kDa. Transferrin is the physiologically appropriate method for providing iron to cells in culture as they facilitate extracellular iron storage and transport. Transferrins have been reported to aid in the cellular uptake of the EVs in vivo, see for instance WO2013084001. In addition and similar to albumin transferrins can aid in the stabilization of the final EV product. In an embodiment, said transferrin is present in the growth medium at a concentration of between 50 mg/l and 100 mg/l, preferably between 55 mg/l and 100 mg/l, preferably between 50 mg/l and 70 mg/l, preferably between 55 mg/l and 70 mg/l. The latter concentration was found optimal for the quality of the EV product.

The current protocol enables the presence of both albumin and transferrin in the end product, where the majority of the albumin and transferrin will be associated with said EVs.

In a further embodiment, said medium is a basic mixture of inorganic metal salts, nutrients such as amino acids, and vitamins, with a pH in the range from pH 7.0 to 7.4, such as known from the composition of Dulbecco's Modified Eagle Medium (DMEM) or DMEM/F-12. The media may also contain glutamine or glutamate, or a precursor thereof such as L-alanyl-L-glutamine, and glucose at a level of not more than 4500 mg/l and one or more fatty acids.

In a further embodiment, said medium further comprises human growth factors, such as but not limited to epidermal growth factor (EGF), fibroblast growth factor (FGF), insulin-like growth factors (IGF), human platelet-derived growth factor (PDGF, such as human PDGF-BB, human PDGF-AB and PDGF-AA) and/or human TGF-β1, preferably recombinant PDGF-BB and/or TGF-β1. The present inventors have also found that the growth factors act synergistically with other growth factors to promote MSC growth and proliferation. In an embodiment, said medium further comprises PDGF and TGF-β1.

PDGF is a regulator of cell growth and division which binds to platelet derived growth factor receptors (PDGFR). In chemical terms, PDGF is a dimeric glycoprotein composed of two A (-AA) or two B (-BB) chains or a combination of the two (-AB). PDGF-AB has been shown to bind PDGF alpha and beta receptor subunits to form PDGF alpha-beta and alpha-alpha receptor dimers. In the context of the present disclosure PDGF encompasses PDGF-BB, PDGF-AB and PDGF-AA.

Transforming growth factor-beta 1 (TGF-β1) is a pleiotropic cytokine that stimulates MSC proliferation, and in addition influences MSCs' immunomodulatory properties and modifies their secretome, either toward pro- or anti-inflammatory properties.

In an example, the PDGF is PDGF-BB. In an example, the level of PDGF-BB is between about 1 ng/ml and 150 ng/ml.

In another example, the level of PDGF-BB is between about 7.5 ng/ml and 120 ng/ml. In another example, the level of PDGF-BB is between about 15 ng/ml and 60 ng/ml. In another example, the level of PDGF-BB is at least about 10 ng/ml. In another example, the level of PDGF-BB is at least about 15 ng/ml. In another example, the level of PDGF-BB is at least about 20 ng/ml. In another example, the level of PDGF-BB is at least about 21 ng/ml. In another example, the level of PDGF-BB is at least about 22 ng/ml. In another example, the level of PDGF-BB is at least about 23 ng/ml. In another example, the level of PDGF-BB is at least about 24 ng/ml. In another example, the level of PDGF-BB is at least about 25 ng/ml. In another example, the level of PDGF-BB is at least about 26 ng/ml. In another example, the level of PDGF-BB is at least about 27 ng/ml. In another example, the level of PDGF-BB is at least about 28 ng/ml. In another example, the level of PDGF-BB is at least about 29 ng/ml. In another example, the level of PDGF-BB is at least about 30 ng/ml. In another example, the level of PDGF-BB is at least about 31 ng/ml. In another example, the level of PDGF-BB is at least about 32 ng/ml. In another example, the level of PDGF-BB is at least about 33 ng/ml. In another example, the level of PDGF-BB is at least about 34 ng/ml. In another example, the level of PDGF-BB is at least about 35 ng/ml. In another example, the level of PDGF-BB is at least about 36 ng/ml. In another example, the level of PDGF-BB is at least about 37 ng/ml. In another example, the level of PDGF-BB is at least about 38 ng/ml. In another example, the level of PDGF-BB is at least about 39 ng/ml. In another example, the level of PDGF-BB is at least about 40 ng/ml.

In another example, the PDGF is PDGF-AB. In an example, the level of PDGF-AB is between about 1 ng/ml and 150 ng/ml. In another example, the level of PDGF-AB is between about 7.5 ng/ml and 120 ng/ml. In another example, the level of PDGF-AB is between about 15 ng/ml and 60 ng/ml. In another example, the level of PDGF-AB is at least about 10 ng/ml. In another example, the level of PDGF-AB is at least about 15 ng/ml. In another example, the level of PDGF-AB is at least about 20 ng/ml. In another example, the level of PDGF-AB is at least about 21 ng/ml. In another example, the level of PDGF-AB is at least about 22 ng/ml. In another example, the level of PDGF-AB is at least about 23 ng/ml. In another example, the level of PDGF-AB is at least about 24 ng/ml. In another example, the level of PDGF-AB is at least about 25 ng/ml. In another example, the level of PDGF-AB is at least about 26 ng/ml. In another example, the level of PDGF-AB is at least about 27 ng/ml. In another example, the level of PDGF-AB is at least about 28 ng/ml. In another example, the level of PDGF-AB is at least about 29 ng/ml. In another example, the level of PDGF-AB is at least about 30 ng/ml. In another example, the level of PDGF-AB is at least about 31 ng/ml. In another example, the level of PDGF-AB is at least about 32 ng/ml. In another example, the level of PDGF-AB is at least about 33 ng/ml. In another example, the level of PDGF-AB is at least about 34 ng/ml. In another example, the level of PDGF-AB is at least about 35 ng/ml. In another example, the level of PDGF-AB is at least about 36 ng/ml. In another example, the level of PDGF-AB is at least about 37 ng/ml. In another example, the level of PDGF-AB is at least about 38 ng/ml. In another example, the level of PDGF-AB is at least about 39 ng/ml. In another example, the level of PDGF-AB is at least about 40 ng/ml.

In another example, the PDGF is PDGF-AA. In an example, the level of PDGF-AA is between about 1 ng/ml and 150 ng/ml. In another example, the level of PDGF-AA is between about 7.5 ng/ml and 120 ng/ml. In another example, the level of PDGF-AA is between about 15 ng/ml and 60 ng/ml. In another example, the level of PDGF-AA is at least about 10 ng/ml. In another example, the level of PDGF-AA is at least about 15 ng/ml. In another example, the level of PDGF-AA is at least about 20 ng/ml. In another example, the level of PDGF-AA is at least about 21 ng/ml. In another example, the level of PDGF-AA is at least about 22 ng/ml. In another example, the level of PDGF-AA is at least about 23 ng/ml. In another example, the level of PDGF-AA is at least about 24 ng/ml. In another example, the level of PDGF-AA is at least about 25 ng/ml. In another example, the level of PDGF-AA is at least about 26 ng/ml. In another example, the level of PDGF-AA is at least about 27 ng/ml. In another example, the level of PDGF-AA is at least about 28 ng/ml. In another example, the level of PDGF-AA is at least about 29 ng/ml. In another example, the level of PDGF-AA is at least about 30 ng/ml. In another example, the level of PDGF-AA is at least about 31 ng/ml. In another example, the level of PDGF-AA is at least about 32 ng/ml. In another example, the level of PDGF-AA is at least about 33 ng/ml. In another example, the level of PDGF-AA is at least about 34 ng/ml. In another example, the level of PDGF-AA is at least about 35 ng/ml. In another example, the level of PDGF-AA is at least about 36 ng/ml. In another example, the level of PDGF-AA is at least about 37 ng/ml. In another example, the level of PDGF-AA is at least about 38 ng/ml. In another example, the level of PDGF-AA is at least about 39 ng/ml. In another example, the level of PDGF-AA is at least about 40 ng/ml.

The xeno-free and serum-free culture medium may be prepared by combining the individual components, or it may be selected (and optionally adapted) from commercially available products based on the guidance provided herein. For example, commercially available xeno-free and serum-free culture media that may potentially be used, optionally after adaptation according to the optional features and/or preferences disclosed herein can be used.

In an embodiment, said medium may be provided with a buffering system. Regulating pH is critical for optimum culture conditions and is generally achieved by one of the two buffering systems, either a natural buffering system or a chemical buffering system.

In a natural buffering system, gaseous $CO_2$ balances with the $CO_3^{--}/HCO_3^-$ content of the culture medium. Cultures with a natural buffering system need to be maintained in an air atmosphere with 5-10% $CO_2$, usually maintained by use of a $CO_2$ incubator. A natural buffering system is low-cost and non-toxic. Chemical buffering using a zwitterion, HEPES, has a superior buffering capacity in the pH range 7.2-7.4 and does not require a controlled gaseous atmosphere. HEPES is relatively expensive and toxic at a higher concentration for some cell types. HEPES has also been shown to greatly increase the sensitivity of media to phototoxic effects induced by exposure to fluorescent light.

In an embodiment, said medium may include phenol red as a pH indicator, which allows constant monitoring of pH. During the cell growth, the medium changes color as pH is changed due to the metabolites released by the cells. At low pH levels, phenol red turns the medium yellow, while at higher pH levels it turns the medium purple. Medium is bright red for pH 7.4, the optimum pH value for cell culture.

In another embodiment, said medium may comprise inorganic salt. Said inorganic salts help to retain the osmotic balance and help in regulating membrane potential by providing sodium, potassium, and calcium ions.

Said medium may include amino acids, preferably essential amino acids. L-glutamine, an essential amino acid, is particularly important. L-glutamine provides nitrogen for NAD, NADPH and nucleotides and serves as a secondary energy source for metabolism. L-glutamine is an unstable amino acid, that, with time, converts to a form that cannot be used by cells, and should thus be added to media just before use. Caution should be used when adding more L-glutamine than is called for in the original medium formulation since its degradation results in the build-up of ammonia, and ammonia can have a deleterious effect on some cell lines. L-glutamine concentrations for mammalian cell culture media can vary from 0.68 mM in Medium 199 to 4 mM in Dulbecco's Modified Eagles's Medium. Invertebrate cell culture media can contain as much as 12.3 mM L-glutamine. Supplements like glutamax are more stable and can replace glutamine for long term culturing with no need of medium change or supplementation, and for more stable glutamine concentration during this period.

Nonessential amino acids may also be added to the medium to replace those that have been depleted during growth. Supplementation of media with non-essential amino acids stimulates growth and prolongs the viability of the cells.

Carbohydrates in the form of sugars are the major source of energy. Most of the media contain glucose and galactose, however, some contain maltose and fructose.

Said medium may further also comprise fatty acids, lipids, vitamins, trace elements. Trace elements are often supplemented to serum-free media to replace those normally found in serum. Trace elements like copper, zinc, selenium and tricarboxylic acid intermediates are chemical elements that are needed in minute amounts for proper cell growth.

In an embodiment, antibiotics may be used to control the growth of bacterial and/or fungal contaminants, such as, typically, mixtures of penicillin and streptomycin, and/or other compounds, exemplified but not limited to, amphotericin, ampicillin, gentamicin, bleomycin, hygromycin, kanamycin, levofloxacine, mitomycin, mycophenolic acid, nalidixic acid, neomycin, nystatin, paromomycin, penicillin, polymyxin, puromycin, rifampicin, spectinomycin, streptomycin, tetracycline, tylosin, and zeocin.

In an embodiment, said MSCs may grow and expand on microcarriers or microbeads present in said bioreactor. Such microcarriers or beads are known in the art and commercially available. In an embodiment, said microcarriers or beads may be coated with an extracellular matrix protein, such as fibronectin, laminin, hyaluronic acid, their mimetics or a combination thereof. In a preferred embodiment, said microcarriers or beads are negatively charged.

Once the MSCs have reached a desired concentration and/or confluency, cell supernatant comprising said EVs is collected for further processing. In the context of the current invention, said cell supernatant is the cell medium in which the MSCs were allowed to grow and expand. In an embodiment, said supernatant is collected when said MSCs reach a minimal concentration of at least $40 \times 10^6$ cells/l. Cell concentration and viability may be defined by means of cell counting, such as for instance by means of a hemacytometer such as Bürker Counting Chamber and trypan blue staining. Under the culturing conditions described above, said MSCs will produce at least $0.25 \times 10^9$ particles/mL cell medium in a time span of 18 to 24 hours of culturing said MSCs.

"Particle" as used above can be any particle having a particle size of preferably between 0.05 and 0.22 micron, among which are EVs. Other examples of particles can be proteins or peptides aggregates. The source of said particles is MSCs or the cell medium for culturing and expanding MSCs. Therefore said particle can be any particle that is normally present or part of said cell medium or MSC.

Preferably, when using the method as described herein, at least 90% of said particles with particle size of between 0.05 and 0.22 micron are EVs.

In a subsequent step, said cell supernatant is to be filtered in order to remove contaminants present in said cell medium. The latter will contribute to the purity and stability of the end-product. In a preferred embodiment, said filtration will comprise at least two steps of filtration. In an embodiment, at least one of said filtration steps will be dead-end filtration. In a further embodiment, said both filtration steps are performed by means dead-end filtration. Preferably, at least one of the filtration steps is also used as a product sterilization means, in order to be compliant with GMP regulations as defined above. Sequential dead-end filtration was in some cases found necessary to sufficiently remove impurities from the supernatant. In some cases, it was found that single filtration often resulted in blockage of the filter used and reduced the purity and quantity of the end product.

In a first filtration step, cell supernatant is filtered through a dead-end filter. In a further preferred embodiment, said filtration occurs by means of bringing said supernatant over a filter with mesh size of between 1 and 5 micron, more preferably between 1 and 3 micron. In an embodiment, said first filtration step is performed by means of dead-end filtration, preferably in a closed system with a peristaltic pump providing constant flow through the filter, preferably at 100 ml/min.

In an embodiment, the filtrate of the first filtration will be brought over a second filter, this time a filter with a pore size that is smaller than the pore size used in the first filtration step. Preferably, this second filtration step is a sterilization step, in order to render the final product compliant with GMP regulations as defined above. In a more preferred embodiment, said filter has a mesh size below 1 micron, more preferably between 0.05 and 1 micron, even more preferably between 0.1 and 0.5 micron, most preferably between 0.1 and 0.22 micron. In an embodiment, said second filtration step is performed by means of dead-end filtration, preferably in a closed system interconnected with the first step of filtration, and with a peristaltic pump providing constant flow through the filter, preferably at 100 ml/min.

The filtrate of said filtration steps will comprise the EVs according to the current invention. In a final step, said EVs will be washed and concentrated. Washing and concentration may occur by conventional means known in the art such as membrane filtration, either micro- or ultrafiltration. Concentration is a process that involves removing fluid from a solution while retaining the solute molecules.

Membrane filtration is a separation technique widely used in the life science laboratory. Depending on membrane porosity, it can be classified as a microfiltration or ultrafiltration process. Microfiltration membranes, with pore sizes typically between 0.1 μm and 10 μm, are generally used for clarification, sterilization, and removal of microparticulates or for cell harvesting. Ultrafiltration membranes, with much smaller pore sizes between 0.001 and 0.1 μm, are used for concentrating and desalting dissolved molecules (proteins, peptides, nucleic acids, carbohydrates, and other biomolecules), exchanging buffers, and gross fractionation. Ultrafiltration membranes are typically classified by molecular weight cutoff (MWCO) rather than pore size. There are two main membrane filtration modes which can use either microfiltration or ultrafiltration membranes: 1) Direct Flow Filtration (DFF), also known as "dead-end" filtration, applies the feed stream perpendicular to the membrane face and attempts to pass 100% of the fluid through the membrane, and 2) Tangential Flow Filtration (TFF), also known as crossflow filtration, where the feed stream passes parallel to the membrane face as one portion passes through the membrane (permeate) while the remainder (retentate) is recirculated back to the feed reservoir.

By preference said washing and concentration will be performed by means of TFF. TFF or Crossflow Filtration is a process where the feed stream flows parallel to the membrane face. Applied pressure causes one portion of the flow stream to pass through a membrane (filtrate or permeate) while the remainder (retentate) is recirculated back to the feed reservoir.

In an embodiment, the filtrate of one or more dead-end filtration steps will be used in a TFF concentration step. In a further preferred embodiment, the TFF will have a cut-off range of 100 kDa and will remove the majority if not all particles and components with a molecular weight lower than 100 kDa into the TFF permeate. Consequently, said final composition, which will remain in the retentate, will be depleted from free (that is: not EV-associated) constituents, components or substances with a molecular weight below 100 kDa. Said constituents, components or substances can be any particle such as a protein or a peptide that is normally present or part of said cell medium. The retentate will be recirculated in the TFF device until the required retentate concentration has been reached. During the recirculation, the retentate can be washed using a washing medium or washing buffer, preferably a saline washing buffer, in order to remove unwanted components. The concentrated retentate can subsequently be collected in a collection vessel, such as but not limited to a collection bag or cryotubes, either kept at low temperature of below 10° C., preferably 4° C., or frozen at −20° C. to −196° C., preferably at −40° C. to −196° C., even more preferably at −80° C. to −196° C.

The EVs of the current invention are derived from MSCs. Said MSCs are human derived and may originate from bone marrow, umbilical cord, Wharton's jelly, cord blood, amniotic membrane, bone marrow, adipose tissue, dental pulp, peripheral blood, fallopian tube, mammary gland, liver and lung tissue. In a preferred embodiment, said MSCs are derived from umbilical cord (UC-MSCs).

In an embodiment, MSCs will be freshly isolated from one of the tissues as described above and further expanded in a bioreactor. In another embodiment, cryopreserved MSCs are being used. Methods for obtaining MSCs from various origin are generally known in the art and are readily applicable to the current invention. In short, tissue such as umbilical cord may be enzymatically digested, e.g. by means of enzymes such as collagenase and/or trypsin, washed and centrifuged. The resulting pellet will subsequently be plated in suitable cell medium in culture flasks while being incubated at the appropriate conditions. Said culture flasks may be coated with an extracellular matrix protein, such as fibronectin, laminin, hyaluronic acid, their mimetics or a combination thereof. The latter may enhance attachment and cell growth. In another embodiment, said culture flasks may comprise coated microcarriers or microbeads, for instance coated with an extracellular matrix protein, such as fibronectin, laminin, hyaluronic acid, their mimetics or a combination thereof. Medium will be refreshed until cells reach a confluency of a predefined minimal percentage, preferably a confluency of more than 80%, after which cells will be harvested.

When passaged, the cultured cells are detached and dissociated from the culture substrate and from each other. Detachment and dissociation of the cells can be carried out as generally known in the art, e.g., by enzymatic treatment with proteolytic enzymes (e.g., chosen from trypsin, collagenase, e.g., type I, II, III or IV, dispase, pronase, papain, etc.), treatment with bivalent ion chelators (e.g., EDTA or EGTA) or mechanical treatment (e.g., repeated pipetting through a small bore pipette or pipette tip), or any combination of these treatments.

A suitable method of cell detachment and dispersion should ensure a desired degree of cell detachment and dispersion, while preserving a majority of viable cells in the culture. Preferably, the detachment and dissociation of the cultured cells would yield a substantial proportion of cells as single, viable cells (e.g., at least 50%, 70%, 80%, 90% of the cells or more). The remaining cells may be present in cell clusters, each containing a relatively small number of cells (e.g., on average, between 1 and 100 cells).

Next, the so detached and dissociated cells (typically as a cell suspension in an isotonic buffer or a medium) may be re-plated onto a substrate which allows the adherence of cells thereto, and are subsequently cultured in a medium as described above sustaining the further proliferation. These cells may then be cultured by re-plating them at a density of between 10 and $10^5$ cells/cm², and at a splitting ratio between about 1/16 and 1/2, preferably between about 1/8 and 1/2, more preferably between about 1/4 and 1/2. The splitting ratio denotes the fraction of the passaged cells that is seeded into an empty (typically a new) culture vessel of the same surface area as the vessel from which the cells were obtained. The type of culture vessel, as well as of surface allowing cell adherence into the culture vessel and the cell culture media, can be the same as initially used and as described above, or may be different.

In a preferred step, cells will subsequently be seeded and expanded in larger recipients. Once the cells have reached a desirable amount, they can directly be brought to a bioreactor for further expansion and EV harvesting, or an appropriate amount of cells can be cryopreserved for later use. Cryoprotection of said MSCs typically occurs in the presence of one or more cryoprotectant agents. These agents prevent cell damage during freezing and thawing and are typically known to the skilled artisan. Example of a cryoprotectant agent is for instance DMSO, mixed with cell medium. The cells may be cryopreserved in thereto suitable containers or cryobags.

In a further step, said MSCs (either freshly isolated or cryopreserved MSCs) may be further expanded in a bioreactor, preferably a closed stirred-tank type bioreactor. Cells will be expanded in the bioreactor in appropriate expansion conditions (serum and xenofree medium) as described above. In an embodiment, the containers or cryobags used for cryopreservation as described above, are designed in a way to be attached to the bioreactor in a sterile way, avoiding the need for a (laminar) flow cabinet. This makes the EVs production process independent from (high-sterility) clean rooms.

The method as described above may be performed in an purification system for EVs, comprising a MSC cell expansion unit and a processing unit for EVs. Both units and their respective compartments and/or components will be fluidly connected with each other, allowing flow of cell medium and material from one unit to another. Fluid connection will be achieved by conventional means in the art, such as tubing, pipes, valves and pumps. In an embodiment, said MSC cell expansion unit will comprise a bioreactor, preferably a stirred-type bioreactor and a cooling compartment. Said cooling compartment will be provided by means for cooling down the ambient temperature and objects in said cooling compartment to a temperature of below 10 degrees such as 4 degrees. In a preferred embodiment, said cooling compartment is a fridge. Said cooling compartment may be provided with tanks or vessels for storing respectively fresh cell culture medium, to be transferred to the bioreactor and cell supernatant coming from said bioreactor. To this purpose, an outlet of the cell culture medium vessel or tank will be fluidly connected with an inlet of the bioreactor. A pump, preferably a peristaltic pump, will be present to ensure correct medium flow. An outlet of the bioreactor will be fluidly connected with an inlet of the cell supernatant vessel in the cooling compartment. Again, a (peristaltic) pump can be present to ensure product flow. By the current set-up, supernatant from the bioreactor may flow to the cell supernatant collecting vessel or tank, while the bioreactor may be supplied with fresh medium. The bioreactor is by preference a stirred bioreactor. Preferably said fresh medium is at least at room temperature or more preferably preheated by any heating device as known in the art, such as an incubator, preferably to around 37° C. Stirring may be achieved by conventional means in the art, for instance by means of a magnetic stirrer or a stirrer installed in said bioreactor. Said bioreactor may be supplied with $CO_2$ or may be located in a $CO_2$ incubator. In the latter embodiment, the bioreactor will be provided by means for allowing gaseous exchange. Sensors may be present in the cell expansion unit to monitor the various processes. In an embodiment, sensors are present to measure the temperature, the humidity and the $CO_2$ level in said bioreactor and/or $CO_2$ incubator. Sensors may also be present to monitor the conditions in the cooling compartment, e.g. to monitor the temperature.

Cell supernatant comprising the EVs will be sourced from the bioreactor once the MSCs have reached the desired amount and will be stored at a temperature below 10° C., such as 4° C. Once an appropriate volume of cell supernatant is obtained, said supernatant will be transferred to the EV processing unit. In an embodiment, this appropriate volume is transferred in batches to the EV processing unit. Different batches can again be pooled before processing. In an alternative embodiment, this volume in transferred continuously to the EV processing unit. The EV processing unit is preferably equipped with one or more filter devices, a membrane filtration device such as a TFF concentrator and a storage compartment for the final product (in order as described herein). These devices and compartments are fluidly connected and allow fluid transport from one device to another, by preference is a closed loop system. In a further preferred embodiment, said EV processing unit comprises a first filter device having a filter mesh size of between 1 and 5 micron, more preferably between 1 and 3 micron. The filtrate of the first filtration will subsequently be transferred to a second filter device, this time having a mesh size that is smaller than the mesh size used in the first filtration step. In a more preferred embodiment, said filter device has a mesh size of below 1 micron, more preferably between 0.05 and 1 micron, even more preferably between 0.1 and 0.5 micron, most preferably between 0.1 and 0.22 micron. In an embodiment, said filter devices allow dead-end filtration, preferably in a closed system interconnected with the first step of filtration, and with a peristaltic pump providing constant flow through the filter, preferably at 100 ml/min.

After filtration, the filtrate is transferred to a TFF device. To that purpose, the final filter device will again be in fluid connection with said TFF. These devices are typically classified by molecular weight cut-off (MWCO). Molecular weight cut-off (MWCO) or nominal molecular weight cutoff (NMWCO) is defined as the minimum molecular weight of a solute that is 90% retained by the membrane. In a preferred embodiment, said TFF will have a cut-off range of 100 kDa. Said TFF will be used to wash, concentrate and further purify the sample. From the TFF the concentrated and purified sample will be transferred to a fill and finish unit for obtaining the final product. In an embodiment, the final product will be collected in a bag, which may be connected to a filling device aliquoting samples into final recipients. Alternatively, the aliquoting into the final recipients can be performed manually.

As an example, when using a production method as described above, at least $1 \times 10^{11}$ particles per ml of the final product composition may be obtained from the 100-fold concentrated supernatant of MSCs which were at a minimal concentration of at least $40 \times 10^6$ cells/l in a bioreactor. MSC confluency was maximum 80%. Preferably about $8 \times 10^6$ MSCs are inoculated per 0.5 l bioreactor, cultured and allowed to fully expand. Subsequently, said MSCs start to release EVs to the supernatant, which is collected in e.g. culture bags, every 24 hours. In this example, the content of four of said culture bags is pooled, and upon filtration (in this example a mesh size of 0.22 micron is used) and 100× concentration, at least $1 \times 10^{11}$ particles per ml are obtained.

"Particle" as used in the above-shown example can be any particle having a particle size of between 0.05 and 0.22 micron, among which are EVs. Other examples of particles can be proteins or peptides aggregates. The source of said particles is MSCs or the cell medium for culturing and expanding MSCs. Therefore said particle can be any particle that is normally present or part of said cell medium or MSC.

Preferably, when using the method as described above, at least 90% of said particles with particle size of between 0.05 and 0.22 micron are EVs.

In a further aspect, the current invention is also directed to a composition comprising EVs derived from MSCs. In a preferred embodiment, said EVs will have a size below 1 μm, and said composition has a human albumin concentration of between 10 and 30 g/l.

In another or further embodiment, a composition according to the current invention comprises EVs derived from MSCs having a size below 1 μm and comprising transferrin and albumin at a ratio of between about 2 and 60 mg transferrin per g albumin, preferably of between about 5 and 55 mg transferrin per g albumin, more preferably of between about 10 and 45 mg transferrin per g albumin, most preferably of between about 10 and 40 mg transferrin per g albumin.

In an embodiment, the EVs of the composition have a size below 1 μm. In a preferred embodiment, the EVs of the composition have a size of about below 750 nm, preferably below 500 nm, preferably below 400 nm, preferably below 300 nm. In another or further preferred embodiment, the EVs of the composition have a size of at least 5 nm, more preferably at least 10 nm, more preferably at least 25 nm, more preferably at least 50 nm. In another or further preferred embodiment, the EVs of the composition have a size of between 25 and 500 nm, preferably between 25 and 400 nm, more preferably between about 50 and about 300 nm.

Optical techniques are routinely used to size and count EVs. In an embodiment of the current invention, the particle size of said EVs is measured by Nanoparticle Tracking Analysis (NTA), which is a preferred method for quantification and sizing of nanoparticles suspended in liquid buffers. In another of further embodiment, the particle size is measured using Tunable Resistive Pulse Sensing (TRPS) which is used as a reference method to NTA. In another or further embodiment, the particle size is measured using High-Resolution Flow Cytometry.

The composition according to the current invention which is obtainable by the process described above will comprise human albumin at a concentration of between 10 and 30 g/l, more preferably at a concentration of between 10 and 20 g/l, more preferably between 15 and 20 g/l, or preferably between 12 and 16 g/l. Said albumin concentration may be measured by means of colorimetric methods or ELISA by means of an anti-albumin antibody. In an embodiment, said colorimetric measurement is a bromocresol green assay.

The source of said albumin is the cell medium for MSCs. While albumin might thus theoretically be considered a contaminant of the production process as it is not produced by the MSCs, it was surprisingly found that the presence of albumin is in fact needed to ensure the stability and functionality of the end-product and thus the composition of the current invention. Albumin at the required concentration acts in part as a drug stabilizer and enhancer of activity. It was found that forced removal of albumin reduces the activity of the product (Hyungtaek Jeon et al., 2020).

Preferably, said albumin is a clinical-grade product in order to be acceptable for use in animals and/or humans.

In an embodiment, at least 90% of said albumin present in said composition is associated with said EVs in said composition.

Human albumin has a MW of about 66 kDa. Albumin not associated with EVs will therefore be removed by TFF treatment, the remaining albumin in the composition being associated with the EVs. In a further preferred embodiment, at least 93%, more preferably 94%, more preferably 95%, more preferably 96%, more preferably 97%, more preferably 98%, more preferably 99% of the albumin in said composition is associated with EV.

In an embodiment, said composition will also comprise human transferrin. The level of transferrin in said composition is preferably between 25 mg/l and 95 mg/l, more preferably between 55 mg/l and 75 mg/l. In an embodiment, the level of transferrin in said composition is preferably between 60 and 600 mg/l, preferably between 100 and 500 mg/l, more preferably between 150 and 450 mg/l. Transferrin has been described to play a role in the particle transfer through the cell membrane and is said to play a role in the stability of EVs and their uptake by cells in vivo. Hence, the presence of transferrin is known to have a positive impact on the further use of said EV composition.

In an embodiment, at least 90% of said transferrin present in said composition is associated with said EVs in said composition.

Human transferrin has a MW of about 80 kDa. Transferrin not associated with said EVs is therefore removed to a certain extent by TFF treatment, the remaining transferrin in the composition being associated with the EVs. In a further preferred embodiment, said at least 93%, more preferably 94%, more preferably 95%, more preferably 96%, more preferably 97%, more preferably 98%, more preferably 99% of the transferrin in said composition is associated with said EVs.

The concentration of both albumin and transferrin as well as other proteins can be measured by conventional means in the art such as ELISA.

In an embodiment, said composition comprises less than 5% of free constituents with a molecular weight lower than 100 kDa.

With the term "free constituents", reference is made to components or constituents in the end-product that are not associated with EVs and thus freely available in the end product.

By ensuring that the composition comprises less than 5% of free constituents with a MW below 100 kDa, which can for example be obtained by TFF filtration with a cutoff value of 100 kDa, it is ensured that the composition is sufficiently-defined and GMP compliant. The majority of constituents in cell growth medium of MSCs has a MW of below 100 kDa. When remaining in the end product, such small constituents can be seen as contaminants and are therefore preferably kept to a minimum. In a further preferred embodiment, said composition has less than 4%, less than 3%, less than 2%, less than 1% free constituents.

In a further embodiment at least 60% of said EVs will comprise Annexin V.

Annexins are calcium dependent phospholipid binding proteins for which association with EVs increases anti-inflammatory properties of EVs. Some annexins, such as Annexin V, are linked with pro-inflammatory activity. However it was shown that association of Annexin V with EVs increased anti-inflammatory activity of EVs. Annexin V has a molecular weight of about 37 kDa.

According to an embodiment of the current invention, the ratio between EV-associated albumin and EV-associated Annexin V will be between 1:4.500 and 1:350.000.

In an embodiment of the invention the composition may further comprise one or more secondary therapeutic agents. As used herein, a therapeutic agent refers to any agent which can be used in the prevention, treatment and/or management of a disease such as those discussed herein. Such agents may be intra-vesicular (e.g. contained within the body of the EVs) or may be associated with the EVs. Suitable therapeutic agents will be known to the skilled person and might include noncoding RNA, miRNA, mRNA, growth factors, pro-angiogenic molecules, cardioprotective enzymes, antibodies, anti-inflammatory molecules, anti-fibrotic molecules, anti-oxidative molecules, pro-neurogenic molecules, anti-viral molecules, etc. In some embodiments, the isolated EVs are used together with a secondary agent. In some embodiments, the secondary agent is a steroid, an antioxidant, or inhaled nitric oxide. In some embodiments, the steroid is a corticosteroid. In some embodiments, the corticosteroid is methylprednisolone or dexamethasone. In some embodiments, the antioxidant is superoxide dismutase.

Certain secondary therapeutic agents used in the treatment or management of certain lung diseases including but not limited to pulmonary hypertension include oxygen, anticoagulants such as warfarin (Coumadin); diuretics such as furosemide (Lasix®) or spironalactone (Aldactone®); calcium channel blockers; potassium such as K-dur®; inotropic agents such as digoxin; vasodilators such as nifedipine (Procardia®) or diltiazem (Cardizem®); endothelin receptor antagonists such as bosentan (Tracleer®) and ambrisentan (Letairis®); prostacyclin analogues such as epoprostenol (Flolan®), treprostinil sodium (Remodulin®, Tyvaso®), and iloprost (Ventavis®); and PDE-5 inhibitors such as sildenafil (Revatio®) and tadalafil (Adcirca®).

Said composition will preferably be formulated as a liquid. Storage may be done by means of vials, IV bags, ampoules, cartridges, inhalers such as liquid inhalers, nebulizers or powder inhalers, and prefilled syringes. Said liquid formulation may, apart from the EVs as active principle or drug product further comprise a variety of compounds to ensure a stable active medication following storage. These include solubilizers, stabilizers, buffers, tonicity modifiers, bulking agents, viscosity enhancers/reducers, surfactants, chelating agents, and adjuvants.

In another embodiment, said composition may be lyophilized or freeze dried. Said lyophilized formulation may be stored in vials, cartridges, inhalers such as liquid inhalers, nebulizers or powder inhalers, dual chamber syringes, and prefilled mixing systems. Before administration, a lyophilized composition is reconstituted as a liquid before being administered. This may be done by combining a liquid diluent with the freeze-dried powder, mixing, then injecting. Reconstitution usually requires a reconstitution and delivery system to ensure that the drug is correctly mixed and administered.

In a preferred embodiment, said composition is aqueous. In one embodiment of the invention the EVs will be formulated as a composition which further comprises a pharmaceutically acceptable carrier. The pharmaceutically acceptable carrier or diluent is chosen wherein the EVs of the invention remain viable and retain their properties. A pharmaceutically acceptable carrier is a pharmaceutically acceptable material, composition or vehicle, such as a liquid or solid filler, diluent, excipient, solvent or encapsulating material, involved in carrying or transporting a prophylactically or therapeutically active agent. Each carrier must be "acceptable" in the sense of being compatible with the other ingredients of the formulation and not injurious to the subject. Some examples of materials which can serve as pharmaceutically acceptable carriers include sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide, magnesium stearate and aluminum hydroxide; pyrogen-free water; isotonic saline; Ringer's solution; ethyl alcohol; phosphate buffer solutions; and other nontoxic compatible substances employed in pharmaceutical formulations.

Storage of said composition may occur at 4° C. or more preferably by cryopreservation wherein said composition is frozen at a temperature of between −20° C. and −196° C., preferably between −40° C. and −196° C., more preferably between −80° C. and −196° C. Said freezing procedure is preferably a snap-freezing or vitrification procedure, ensuring that the product remains viable during the freezing process and after thawing. Another freezing procedure can be controlled rate freezing, preferably with compensation of the exothermic reaction at the crystallization point for better product stability. For the latter procedure, a controlled rate freezer can be used.

In an embodiment, said composition will be suitable for administration via injection, intravenous administration, inhalation, intratracheal infusion, systemic infusion, intranasal infusion. Said composition may also be formulated to be used externally, alone or in combination with hydrogels, polymers or polymer medical devices for slow release of EVs.

In some embodiments, the composition is suited for intravenous administration. In some embodiments, the composition is suited for administration to lungs or trachea of a subject. In some embodiments, the composition is formulated for administration by inhalation. In some embodiments, the composition is formulated for administration as an aerosol. In some embodiments, the isolated EVs are administered using a nebulizer. In some embodiments, the isolated EVs are administered using an intratracheal tube.

In some embodiments, the isolated EVs are administered or formulated with a surfactant, preferably a pulmonary surfactant. This surfactant preferably is chosen in such way as not to affect the stability of the composition. In some embodiments, the pulmonary surfactant is isolated naturally occurring surfactant. In some embodiments, the pulmonary surfactant is derived from bovine lung or porcine lung. In some embodiments, the pulmonary surfactant is a synthetic surfactant. A pulmonary surfactant is a lipoprotein mixture useful in keeping lung airways open (e.g., by preventing adhesion of alveolar walls to each other). Pulmonary surfactants may be comprised of phospholipids such as dipalmitoylphosphatidylcholine (DPPC), phosphotidylcholine (PC), phosphotidylglycerol (PG); cholesterol; and proteins such as SP-A, B, C and D. Pulmonary surfactants may be derived from naturally occurring sources such as bovine or porcine lung tissue. Examples include Alveofact™ (from cow lung lavage), Curosurf™ (from minced pig lung), Infasurf™ (from calf lung lavage), and Survanta™ (from minced cow lung, with additional components including DPPC, palmitic acid, and tripalmitin). Pulmonary surfactants may also be synthetic. Examples include Exosurf™ (comprised of DPPC with hexadecanol and tyloxapol), Pumactant™ or Artificial Lung Expanding Compound (ALEC) (comprised of DPPC and PG), KL-4 (comprised of DPPC, palmitoyl-oleoyl phosphatidylglyercol, palmitic acid, and synthetic peptide that mimics SP-B), Venticute™ (comprised of DPPC, PG, palmitic acid, and recombinant SP-C). Pulmonary surfactants may be obtained from commercial suppliers.

The invention also encompasses a packaged and labelled pharmaceutical product. This article of manufacture or kit includes the appropriate unit dosage form in an appropriate vessel or container such as a glass vial or plastic ampoule or other container that is hermetically sealed. The unit dosage form should be suitable for pulmonary delivery for example by aerosol. Preferably, the article of manufacture or kit further comprises instructions on how to use including how to administer the pharmaceutical product. The instructions may further contain informational material that advises a medical practitioner, technician or subject on how to appropriately prevent or treat the disease or disorder in question. In other words, the article of manufacture includes instructions indicating or suggesting a dosing regimen for use including but not limited to actual doses, monitoring procedures, and other monitoring information.

As with any pharmaceutical product, the packaging material and container are designed to protect the stability of the product during storage and shipment, and may contain desiccants to ensure stability.

The kits may include EVs in sterile aqueous suspensions that may be used directly or may be diluted with normal saline for intravenous injection or use in a nebulizer, or dilution or combination with surfactant for intratracheal administration. The kits may therefore also contain the diluent solution or agent, such as saline or surfactant. The kit may also include a pulmonary delivery device such as a nebulizer or disposable components therefore such as the mouthpiece, nosepiece, or mask.

In a final aspect, the current invention equally relates to the use of the composition as described above. More specifically, said composition is suited for therapeutic or prophylactic use. The invention contemplates preventing and treating certain diseases. Preventing a disease means reducing the likelihood that the disease manifests itself and/or delaying the onset of the disease. Treating a disease means reducing or eliminating the symptoms of the disease. The current invention therefore also contemplates providing a method for treating and/or preventing a disease in a subject.

The subjects are preferably human subjects, but certain aspects of the current invention may be performed on any subject likely to derive benefit therefrom, including human subjects, agricultural livestock (e.g., cows, pigs, etc.), prized animals (e.g., horses), companion animals (e.g., dogs, cats, etc.), and the like. In a preferred embodiment, said subject is a human, preferably a human patient, said patient may be an adult, an infant or a neonate.

In an embodiment, the composition according to any of the embodiments above is used in the prevention or treatment of lung disorders. In an embodiment, said lung disorder may be an inflammatory lung disease, lung vascular disease, or acute lung injury. More preferably, said inflammatory lung disease is pulmonary hypertension which is also referred to as pulmonary artery hypertension (PAH), asthma, bronchopulmonary dysplasia (BPD), allergy, idiopathic pulmonary fibrosis or pneumonia. Said inflammatory lung disease may be caused by an infection, such as a viral infection. In a preferred embodiment, said viral infection is influenza, SARS-CoV-1, MERS, or SARS-CoV-2. In another embodiment, said acute lung injury is linked with sepsis or is acute respiratory distress syndrome (ARDS).

These diseases also include lung vascular diseases which may not have an inflammatory component. Still other pulmonary conditions that may be treated according to the invention include acute lung injury which may be linked with sepsis or with ventilation. An example of this latter condition is acute respiratory distress syndrome.

Pulmonary hypertension is a lung disease characterized by blood pressure in the pulmonary artery that is far above normal levels. Symptoms include shortness of breath, chest pain particularly during physical activity, weakness, fatigue, fainting, light headedness particularly during exercise, dizziness, abnormal heart sounds and murmurs, engorgement of the jugular vein, retention of fluid in the abdomen, legs and ankles, and bluish coloring in the nail bed.

Bronchopulmonary dysplasia is a condition that afflicts neonates who have been given oxygen or have been on ventilators, or neonates born prematurely particularly those born very prematurely (e.g., those born before 32 weeks of gestation). It is also referred to as neonatal chronic lung disease. Causes of BPD include mechanical injury for example as a result of ventilation, oxygen toxicity for example as a result of oxygen therapy, and infection. The disease may progress from non-inflammatory to inflammatory with time. Symptoms include bluish skin, chronic cough, rapid breathing, and shortness of breath. Subjects having BPD are more susceptible to infections such as respiratory syncytial virus infection. Subjects having BPD may develop pulmonary hypertension.

Acute respiratory distress syndrome (ARDS), also known as respiratory distress syndrome (RDS) or adult respiratory distress syndrome is a condition that arises as a result of injury to the lungs or acute illness. The injury to the lung may be a result of ventilation, trauma, burns, and/or aspiration. The acute illness may be infectious pneumonia or sepsis. It is considered a severe form of acute lung injury, and it is often fatal. It is characterized by lung inflammation, impaired gas exchange, and release of inflammatory mediators, hypoxemia, and multiple organ failure. ARDS can also be defined as the ratio of arterial partial oxygen tension ($PaO_2$) as a fraction of inspired oxygen ($FiO_2$) below 200 mmHg in the presence of bilateral infiltrates on the chest x-ray. A $PaO_2/FiO_2$ ratio less than 300 mmHg with bilateral infiltrates indicates acute lung injury, which is often a precursor to ARDS. Symptoms of ARDS include shortness of breath, tachypnea, and mental confusion due to low oxygen levels.

Idiopathic pulmonary fibrosis is characterized by scarring or thickening of the lungs without a known cause. It occurs most often in persons 50-70 years of age. Its symptoms include shortness of breath, regular cough (typically a dry cough), chest pain, and decreased activity level.

Prevention and/or treatment may involve in some instances use of the EVs alone or together with one or more secondary agents or active ingredients. Subjects may also be subjected to mechanical interventions such as ventilation with or without exogenous oxygen administration.

The subjects may be those that have a lung disease (or condition) amenable to treatment using the EVs of the invention, or they may be those that are at risk of developing such a disease (or condition). Such subjects include neonates and particularly neonates born at low gestational age. As used herein, a human neonate refers to an human from the time of birth to about 4 weeks of age. As used herein, a human infant refers to a human from about the age of 4 weeks of age to about 3 years of age. As used herein, low gestational age refers to birth (or delivery) that occurs before a normal gestational term for a given species. In humans, a full gestational term is about 40 weeks and may range from 37 weeks to more than 40 weeks. Low gestational age, in humans, akin to a premature birth is defined as birth that occurs before 37 weeks of gestation. The invention therefore contemplates prevention and/or treatment of subjects born before 37 weeks of gestation, including those born at even shorter gestational terms (e.g., before 36, before 35, before 34, before 33, before 32, before 31, before 30, before 29, before 28, before 27, before 26, or before 25 weeks of gestation). Typically such premature infants will be treated as neonates, however the invention contemplates their treatment even beyond the neonate stage and into childhood and/or adulthood. Certain subjects may have a genetic predisposition to certain forms of lung disease such as for example pulmonary hypertension, and those subjects may also be treated according to the invention.

With respect to neonates and particularly low gestation age neonates, the invention contemplates administration of EVs within 4 weeks, 3 weeks, 2 weeks, 1 week, 6 days, 5 days, 4 days, 3 days, 2 days, 1 day, 12 hours, 6 hours, 3 hours, or 1 hour of birth. In some important instances, the MSC exosomes are administered within 1 hour of birth.

The disclosure further contemplates administration of EVs even in the absence of symptoms indicative of a lung disease such as but not limited to BPD.

In an embodiment, said composition comprising EVs according to the current invention may be used in treatment of COVID-19, more specifically COVID-19 induced or acute pneumonia. COVID-19, a novel infectious disease caused by severe acute respiratory syndrome, attacking the human respiratory system and lung's epithelial tissue. It has been reported that a subpopulation of patients is at higher risk of developing more severe symptoms of COVID-19 disease. Major complications include pneumonia, acute respiratory distress syndrome (ARDS), multi-organ failure, septic shock, and death.

It has been shown that COVID-19, also referred to as or caused by SARS-CoV-2, is related to different mechanisms of lung infections that can progress to acute respiratory distress syndrome (ARDS) likely precipitated by a cytokine storm, multi-organ failure, septic shock, and blood clots. In comparison to bacterial pneumonia, which is a common lung infection where the entire lung or a section of the lungs' air sacks become inflamed and are filled with fluid, pus, and cellular debris and is mostly caused by viruses, fungi, or bacteria and often treated with antibiotics. In other cases, cardiovascular complications occur, elevated liver enzymes reflecting liver injury, neurologic manifestations. In children, if the infection progresses, it develops pediatric multisystem inflammatory syndrome, which has symptoms similar to Kawasaki disease, which could resulting in death. Based on the current data, children make up a small proportion of reported cases, with about 1% of cases being under years and 4% aged 10-19 years.

Said composition comprising EVs provides a multi-target therapeutic effect with their main mode of action being the inhibition of an inflammatory process.

The EVs target multiple mechanisms of lung injury including hyper-inflammation and cytokine storm, fibrosis, oxidative stress caused by (mechanical) ventilation and epithelial cells apoptosis due to viral activity and inflammatory reaction.

In another embodiment, said composition comprising EVs is used as a supplementary treatment of COVID-19, more specifically COVID-19 induced or acute pneumonia.

In another embodiment, said composition according to any of the embodiments above is used in the prevention or treatment of inflammatory bowel diseases (IBD) such as Crohn's Disease or ulcerative colitis. IBD are a collection of diseases that result in an inflammation of the gastrointestinal (GI) tract, and the two most common IBD are ulcerative colitis (UC) and Crohn's disease (CD). UC is a disease that causes long-lasting inflammation and sores in the innermost lining of the colon and rectum. CD can develop anywhere in the digestive tract and can penetrate into the deep layers of the affected tissue. A symptom of CD is the development of perianal fistulas. The diseases are similar, however, in that both can cause abdominal pain, severe diarrhea, fatigue and weight loss.

In case of administration of EVs in the context of a lung disease, the preferred way of administration will be intratracheal infusion or inhalation. In the context of neurology diseases, this will preferably be systemic infusion, intranasal infusion or inhalation. In the context of Crohn's disease fistulas, ulcers or cartilage repair, this will preferably be via local injection(s). In the case of treatment of wound healing, burns and/or ulcers, the EVs will preferably be administered at the external side of the body, preferably in combination with hydrogels or polymer medical devices for slow release of EVs.

The EVs of the invention are administered in effective amounts. An effective amount is that amount of an agent that alone stimulates the desired outcome. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation. Dosage may also differ depending on the subject to which said composition is administered.

In an embodiment of the current invention, said EVs are administered at a dose of $10^9$ EVs/kg to $10^{12}$ EVs/kg of said patient, or at a dose of $10^{10}$ EVs/kg to $10^{12}$ EVs/kg of said patient. In a further embodiment, dosage ranges from $10^9$ EVs/kg to $10^{11}$ EVs/kg in children (from the age of 0 months to 12 year). In teenagers and adults, said dose may range from $10^9$ EVs/kg to $10^{12}$ EVs/kg in adults.

In an embodiment of the current invention, said EVs are administered at a dose of about $10^{10}$ to about $10^{12}$ EVs per patient for the treatment of CD perianal fistulas.

The disclosure also contemplates repeated administration of EVs, including two, three, four, five or more administrations. In some instances, said EVs may be administered continuously. Repeated or continuous administration may occur over a period of several hours (e.g., 1-2, 1-3, 1-6, 1-12, 1-18, or 1-24 hours), several days (e.g., 1-2, 1-3, 1-4, 1-5, 1-6 days, or 1-7 days) or several weeks (e.g., 1-2 weeks, 1-3 weeks, or 1-4 weeks) depending on the severity of the condition being treated. If administration is repeated but not continuous, the time in between administrations may be hours (e.g., 4 hours, 6 hours, or 12 hours), days (e.g., 1 day, 2 days, 3 days, 4 days, 5 days, or 6 days), or weeks (e.g., 1 week, 2 weeks, 3 weeks, or 4 weeks). The time between administrations may be the same or they may differ. As an example, if the symptoms of the disease appear to be worsening the EVs may be administered more frequently, and then once the symptoms are stabilized or diminishing the EVs may be administered less frequently.

In some instances, repeated intravenous administration of low doses of EVs may occur. Accordingly, the disclosure contemplates repeated administration of low dosage forms of EVs as well as single administrations of high dosage forms of EVs. Low dosage forms may range from, without limitation, $10^{10}$-$10^{11}$ EVs per kilogram or per local infusion, while high dosage forms may range from, without limitation, $10^{11}$-$10^{12}$ per kilogram or per local infusion. It will be understood that, depending on the severity of the disease, the health of the subject, and the route of administration, inter alia, the single or repeated administration of low or high dose EVs are contemplated.

The EVs may be administered by any route that effects delivery to the lungs or the gastrointestinal tract. Systemic administration routes such as intravenous bolus injection or continuous infusion are suitable. More direct routes such as intranasal administration, intratracheal administration (e.g., via intubation), and inhalation (e.g., via an aerosol through the mouth or nose) are also contemplated by the invention and in some instances may be more appropriate particularly where rapid action is necessary. As used herein, an aerosol is a suspension of liquid dispersed as small particles in a gas, and it includes a fine mist or a spray containing such particles. As used herein, aerosolization is the process of producing of an aerosol by transforming a liquid suspension into small particles or droplets. This may be done using an aerosol delivery system such as a pressurized pack or a nebulizer. Nebulizers include air-jet (i.e., pneumatic), ultrasonic, and vibrating-mesh nebulizers, for example with the use of a suitable propellant such as but not limited to dichlorodifluoromethane, trichlorofluoromethane, dichlorotetrafluoroethane, carbon dioxide or other suitable gas. In addition to nebulizers, other devices for pulmonary delivery include but are not limited to metered dose inhalers (MDIs) and dry powder inhalers (DPIs). Capsules and cartridges of for example gelatin for use in an inhaler or insufflator may be formulated containing lyophilized exosomes and a suitable powder base such as lactose or starch.

The EVs, when it is desirable to deliver them systemically, may be formulated for parenteral administration by injection, including for example by bolus injection or continuous infusion. Formulations for injection may be presented in unit dosage form, e.g., in ampoules or in multi-dose containers, with or without an added preservative.

The compositions may take such forms as water-soluble suspensions, solutions or emulsions in oily or aqueous vehicles, and may contain formulation agents such as suspending, stabilizing and/or dispersing agents. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or agents which increase solubility. Alternatively, the exosomes may be in lyophilized or other powder or solid form for constitution with a suitable vehicle, e.g., sterile pyrogen-free water, before use.

The EVs and the composition as described herein will preferably be obtained my means of the methodology as described above.

The present invention will be now described in more details, referring to examples that are not limitative.

EXAMPLES AND/OR DESCRIPTION OF FIGURES

Example 1—Isolation of the EVs from MSCs

Umbilical cord (UC) derived MSCs, obtained from umbilical cord tissue or Wharton's Jelly was expanded in an expansion unit, comprising a stirred bioreactor (2) in fluid connection with a cell culture medium supply vessel (1). Reference is made to FIG. 1, wherein the following numbers refer to:

1. Cell culture medium vessel
2. Stirred bioreactor
3. Cell supernatant vessel
4. Refrigerator
5a, 5b, 5c. Peristaltic pumps
6. First filter unit
7. Second filter unit
8. TFF cassette
9. Final product The cells are multiplied in the presence of three-dimensional microcarriers present in said bioreactor (2) and in the presence of a xeno- and serum-free medium comprising purified human albumin at a concentration of 3 g/l. The medium further comprised recombinant purified transferrin at a concentration of 60 mg/l.

The MSCs were allowed to expand and grow until a minimal concentration of at least $40 \times 10^6$ cells/L in the bioreactor (2) was obtained and MSC confluency was maximum 80%. Cell concentration was defined by means of cell counting and fluorescent labelling of MSC adherent to microbeads. At this stage, the cells were ready to start EVs secretion. For this purpose fresh serum-free and xeno-free medium was diluted with basal medium (DMEM/high glucose/no phenol-red/glutamax, Thermo Scientific) 1:10 and supplied to the cell culture. After 24 hrs, the system was ready to start harvesting the EVs. For this purpose, conditioned cell medium or cell supernatant from the bioreactor (2) was pumped to a cell supernatant vessel (3), present in a refrigerator (4) set at 4° C. This supernatant comprised EVs, produced by the MSCs. Supernatant collected in the vessel (3) was subsequently pumped by means of a peristaltic pump (5c) to a first filter unit (6) having a 2 micron filter. The supernatant was filtered by means of dead-end filtration in a closed system with a peristaltic pump (5c) providing constant flow through the filter (6) at 100 ml/min. The flow-through of the first filtration step was subsequently filtered in a second filter unit (7), which was in fluid connection with the first filter unit (6), having a 0.2 micron filter. Filtration was by means of dead-end filtration in a closed system with a peristaltic pump (5c) providing constant flow through the filter (7) at 100 ml/min. Flow through comprising the EVs was collected into a 11 bag, and subsequently stored at 4° C.

In a final step, said flow-through was brought over a TFF cassette (8) having 100 kDa cutoff, which was in fluid connection with the dead-end filter units (6, 7). The retentate of the TFF cassette (8) comprising the EVs was washed with saline buffer solution and concentrated by circulation through the TFF cassette (8) using a peristaltic pump (5c), which has a rotator speed of 300 rpm, to final volume of 10 ml. The final product (9) was collected from the TFF (8) and either frozen at −80° C. or below, or kept at 4° C. in cryotubes, bags or other appropriate vessels.

The final product was analyzed to ensure the quality of said product. Quality control included measurement of the concentration of albumin associated with EVs to ensure the purity and the stability of said product by means of colorimetric analysis and ELISA, particle analysis by means of techniques such as Nanoparticle Tracking Analyzer (NTA), Tunable Resistive Pulse Sensing (TRPS), electron microscopy and/or RAMAN microscopy. A sample of the product was tested for the presence of endotoxins and/or mycoplasma. Other quality controls included qualitative chromatography, mass spectrometry, ELISA, sequencing, qRT-PCR and activity tests such as in vitro T-, B-cells and macrophage polarization.

Under the culturing conditions described above, said MSCs will produce at least $0.25 \times 10^9$ particles/ml cell medium in a time span of 18 to 24 hours of culturing said MSCs.

The experiment was performed with MSCs derived from UCs but has also been repeated by MSCs originating from other tissue or origin, including but not limiting to mammary gland, bone marrow, Wharton's jelly, (cord) blood, peripheral blood, amniotic membrane, adipose tissue, dental pulp, fallopian tube, liver and lung tissue.

Example 2: Measuring the Albumin Concentration in the EV Product

The EV product obtained via the method as described in example 1 was analyzed for albumin concentration. The albumin concentration was measured using two different methods:

Colorimetric measurement
ELISA

In short, bromocresol green was used to evaluate the albumin concentration in the sample by means of colorimetric reaction. ELISA concentration measurements were used by means of an anti-human albumin antibody.

The albumin concentration measured in the final product by means of colorimetric reaction was 16 g/l. The concentration measured by means of ELISA was approx. 17 g/L.

Albumin has a MW of approx. 66 kDa and any albumin, which is not associated with the EVs, is expected to be removed by the 100 kDa cut-off TFF. The remaining albumin is therefore considered associated with EVs.

Example 3: Measuring the Transferrin Concentration in the EV Product

The EV product obtained via the method as described in example 1 is analyzed for transferrin concentration. The transferrin concentration is quantified using ELISA (Abcam) following the manufacturer protocol.

Transferrin concentration measured in the final product by ELISA (Abcam) was 70 mg/l.

Example 4: Purity of Clinical-Grade Culture Medium for EVs Production

An experiment is performed to evaluate the concentration of contaminating particles in different media used for EVs production. The following media are tested:
1. xeno-free and serum free medium with 0.3 g/l purified human albumin and 7 mg/l recombinant purified transferrin (about 1:10 diluted using DMEM medium compared to the medium used in Example 1)
2. basal DMEM medium without supplements (Thermo Scientific/Lonza)
3. culture medium supplemented with undefined products (Thermo Scientific/Lonza)

Samples of fresh media are analyzed using NTA, TRPS, and FACS devices. Particles sizes and quantity are quantified. Purified water is used as control.

EVs are produced via the method as described in example 1, and with one of the media described above. Quality control results indicate that for EVs produced in the different media, the lowest number of contaminating particles is in medium 2, however this medium does not support long-term cell culture. Highest number of contaminating particles is in medium 3. Medium 1 has a number of contaminating particles in between the other media, but does support a long-term cell culture.

Example 5: Cell Culture in Clinical-Grade Medium for EVs Production

This experiment demonstrates cell number, cell growth curve and cell viability in:
1. xeno-free and serum-free medium with 3 g/l purified human albumin and 60 mg/l recombinant purified transferrin (similar medium as used in Example 1)
2. basal DMEM medium without supplements (Thermo Scientific/Lonza)
3. culture medium supplemented with undefined products (Thermo Scientific/Lonza)

Method

In a first experiment, MSCs are expanded in a culture system as described above in the first example, in the presence of media 1, 2 or 3 until the cells reach 70-80% confluency.

Subsequently, in the second experiment the cells which were expanded in the first experiment in media 1, 2, and 3 are refreshed using the same media.

In the third experiment, the cells which were expanded in the first experiment in medium 1 will be refreshed with the medium 1 mixed with the medium 2 in the ratio 2:8. In the same experiment the cells which were expanded in the first experiment in medium 3 will be refreshed with the medium 3 mixed with the medium 2 in the ratio 2:8.

In the fourth experiment, the cells which were expanded in the first experiment in media 1, 2 and 3 will be refreshed with the medium 2.

In the experiments 2, 3 and 4 cell cultures are continued for at least 5 days and the media were refreshed every 24 hrs. Medium refreshment is performed by removal of 100% of the old medium and adding the same volume of the corresponding fresh medium.

Results

The first experiment confirms that MSC in medium 1 and 3 attach to the microcarriers whereas this is not the case for medium 2. MSCs are able to grow/expand in both media 1 and 3 but do not remain viable medium 2. Only the cells cultured in media 1 and 3 are used in subsequent experiments.

In the experiments 2 cell cultures in undiluted media 1 and 3 overgrow quickly, within 24-48 hrs, and subsequently the cells die. In the experiments 3 cell cultures with diluted media 1 and 3 keep growing very slowly and cells remain viable for at least 5 days. In the experiment 4 cell cultures where media 1 and 3 were replaced with medium 2 survive only 2 days and subsequently the cells die.

Example 6: EVs Concentration and Efficiency in Clinical-Grade Culture Medium The experiment demonstrates the concentration of EVs in:
1. xeno-free and serum-free medium with 0.3 g/l purified human albumin and 7 mg/l recombinant purified transferrin (about 1:10 diluted using DMEM medium compared to the medium used in Example 1)
2. basal DMEM medium without supplements (Thermo Scientific/Lonza)
3. culture medium supplemented with undefined products (Thermo Scientific/Lonza)

MSCs are expanded as described above and in one of the media as described above. Cultures are continued for at least 5 days and all media is refreshed every 24 hrs.

The EV production protocol of examples 1 and 5 is used. Medium 1 gives the highest concentration of cell-secreted particles (bona fide EVs) calculated as total particles minus particles present in fresh medium. In particular in this example, at least 95%, and up to 99% of the particles have been secreted by the MSCs (EVs).

Example 7: EVs Production Efficiency in 3D Bioreactor System

The experiment is demonstrating the efficiency of EVs production in:
i) 3D culture system as shown in FIG. 1 and described in example 1
ii) a 2D culture system MSCs are produced in 3D culture system (0.5 l and 1 l stirring bioreactors) and in 2D multilayer flasks using medium (i) for expansion followed by diluted medium (i) for EVs production. Cell number, medium volume, footprint, and EVs yield are calculated and extrapolated to larger volumes bioreactors. The 3D bioreactor method provides a lower footprint, lower medium consumption and higher EV yield per batch when comparing to 2D culture system.

Example 8: EVs Isolation Efficiency Using TFF System

This experiment demonstrates the efficiency of EVs purification using:
i) TFF system as final concentration step, with cutoff of 100 kDa
ii) size exclusion chromatography
iii) ultracentrifugation.

The use of the TFF concentration provides significantly higher EV recovery when being compared to SEC. The TFF yield is comparable to the UC yield but the EVs are damaged in the latter one and thus of inferior quality. Moreover, UC is not suited for GMP/large-volume production.

Example 9: EVs Activity in In Vitro Assays for Intended Use in Treatment of BPD

EVs were produced according to example 1 and are used in the treatment of major symptoms of BPD:

a) Inflammation

EV internalization assay. Fluorescently-labelled EVs are co-cultured with human peripheral blood mononuclear cells (PBMCs). Flow cytometry is performed to quantify populations of immune cells with internalized labelled EVs. The following markers are investigated: anti-CD4, anti-CD8, anti-CD11c, anti-CD14, anti-CD19, anti-CD56 and anti-CD15. Analysis is performed after 0-1-6-12-24 hrs and after 6 hrs for neutrophils. EVs produced by fibroblasts are used as negative control.

Lymphocyte migration assay. EVs are co-cultured with PBMC in a trans-well system. Cell migration is investigated towards SDF-1 chemokine. Cell phenotypes and quantification are performed with flow cytometry.

B cell assay. EVs are co-cultured with CpG-stimulated human peripheral blood mononuclear cell. Cell proliferation and differentiation to plasma cells are investigated, phenotypes and quantification are performed with flow cytometry. Quantification of cytokines and antibodies are performed with ELISA.

T cell assay. EVs are co-cultured with human peripheral blood mononuclear cell and T cell activator CD3/CD28 beads. CD4+ T cell proliferation and CD4+ T cell apoptosis are quantified using flow cytometry. Treg/Teff ratio is calculated. Treg proliferation is quantified using flow cytometry. Quantification of following cytokines are performed with ELISA: IL10, TGF-β, galectin-1, HGF, PGE2, GM-CSF, IL2, TNF-α, IFN-γ.

CD cells assay: CD cell activation is investigated in co-culture with EVs using flow cytometry. Upregulation of co-stimulatory molecules CD80 and CD86 and maturation marker CD83 were quantified using flow cytometry. Quantification of following cytokines are performed with ELISA: IL6, IL8, IL12, CCL3, CCL4, IL10, TGF-β. Phagocytosis assay is performed (incubation with FITC-dextran) using flow cytometry. Migration assay is performed using trans-well assay and flow cytometry.

Macrophage assay. EVs are co-cultured with M1-stimulated (LPS) and M2-stimulated (IL4/IL13) macrophages. M1 to M2 ration is calculated using flow cytometry. Quantification of following cytokines are performed with ELISA: IL6, TNFα, IFNγ, IL1β, IL12, IL10, VEGF, MCP1, TGF-β, FGF and confirmed with qPCR gene expression analysis. Trans-well migration assay (towards fMLP) is performed and quantified using flow cytometry.

NK-cell assay. EVs are co-cultured with PBMC derived NK cells. Quantification of following cytokines are performed with ELISA: TNFα, IFNγ. Maturation markers CD27, CD11b, CD107a, IFN-γ and cell proliferation are quantified using flow cytometry.

b) Fibrosis

Experiments are performed using commercial fibrosis assay with normal human lung fibroblasts and human epithelial cells. Human lung fibroblasts are co-cultured with EVs delivered at different timepoints, with multiple doses and different concentrations. Subsequently, analyses of alpha-SMA and collagen I/fibronectin are performed.

In another experiment the EVs influence on epithelial-to-mesenchymal transition (EMT) in primary human bronchial epithelial cells is measured. EMT is investigated using commercial assays following the manufacturer protocol. In one experiment the experimental primary cells derived from healthy tissue or from idiopathic pulmonary fibrosis patients are stimulated with TGF-β to induce EMT, and non-stimulated cells are used as control. Subsequently, human epithelial cells are co-cultured with EVs delivered at different timepoints, with multiple doses and different concentrations. EMT is detected and quantified using FACS and E-cadherin and fibronectin expression.

In another experiment the EVs influence on fibroblasts-to-myofibroblasts transition (FMT) in primary human bronchial fibroblasts cells is measured. FMT is investigated using commercial assays following the manufacturer protocol. In one experiment the experimental primary cells derived from healthy tissue or from idiopathic pulmonary fibrosis patients are stimulated with TGF-β to induce FMT, and non-stimulated cells are used as control. Subsequently, human fibroblast cells are co-cultured with EVs delivered at different timepoints, with multiple doses and different concentrations. FMT is detected and quantified using alpha-smooth muscle actin marker.

c) Oxidative Stress and Cell Apoptosis

Assays and cell lines described for investigation of fibrosis are used for quantification of cell apoptosis and oxidative stress (ELISA, flow cytometry).

Oxidative stress is induced using $H_2O_2$ or other reagents. Cells are exposed to the oxidative stress during different time periods, also different doses of the oxidative stress inducers are used. Subsequently, cells are co-cultured with EVs delivered at different timepoints, with multiple doses and different concentrations. Direct effects of oxidative stress are measured by detection and quantification of reactive oxygen species (ROS) and indirect effects by measuring nucleic acids damage, lipids peroxidation and protein oxidation. Detection and quantification of direct and indirect markers of oxidative stress will be performed using ELISA and FACS.

Cell apoptosis in response to the oxidative stress will be detected and quantified using commercial assays following the manufacturer protocol. In one experiment LIVE/DEAD™ (ThermoFisher) will be used for detection of cell viability using FACS.

In other experiment, Annexin V immunofluorescent staining will detect an early apoptosis and will be quantified using FACS.

In other experiment, an early apoptosis will be detected by quantification of the activated caspase-3 and caspase-7 using FACS.

Example 10: EVs Activity in In Vitro Assays for Intended Use in Treatment of Crohn's Disease The experiments are demonstrating the activity of EVs produced according to example 1 in the treatment of major symptoms of Crohn's disease. In addition to the experiments described in example 9 (a)-(c) also an angiogenesis assay is performed using EVs.

In one experiment EVs are co-cultured with HUVEC cells on Matrigel and tube formation is investigated. Experiments will be performed using commercial angiogenesis tube formation assay using human HUVEC cells. Cells will be cultivated in 3D environment i.e. hydrogel to mimic natural extracellular matrix properties necessary for blood vessels formation. EVs are delivered at different timepoints, with multiple doses and different concentrations. Analysis will be performed using immunolabelling and fluorescent labelling of HUVEC cells and tubes length and branching measurement in response to EVs.

Example 11: EV Biodistribution Study in In Vivo
Models of BPD

The experiment assesses the biodistribution of EVs produced according to example 1 in an in vivo model of BPD.

In vivo non-clinical studies are conducted using a well-established, widely used animal model for the BPD, i.e. newborn rats exposed to hyperoxia (O'Reilly M et al, 2014; Thébaud B, 2018). This model mimics the condition of the artificially ventilated premature baby, since newborn rats have structurally immature lungs (late canalicular/early saccular stage) at birth, reaching the alveolar stage only at postnatal day 5. Rats reach complete alveolarization around postnatal day 30, and exposing a rat born at term to hyperoxia in the early postnatal period is known to disrupt alveolar development, increase alveolar macrophages, and negatively affect pulmonary vascularization. Thus, from a structural point of view, the lungs of newborn term rodent are approximatively equivalent to 24-28-week preterm human newborns (Porzionato A et al, 2019; Porzionato A et al, 2021).

The assessment of the biodistribution of the EV product administered intratracheally (IT) in the newborn rat model of BPD induced by hyperoxia is performed as follows.

The product's EVs are stained with a lipophilic fluorescent marker (DiR iodide [1,1-dioctadecyl-3,3,3,3-tetramethylindotricarbocyanine iodide]) to assess product biodistribution after in vivo administration.

A total of 40 wild-type Sprague-Dawley rat pups is used of which 20 have been exposed to normoxia while the remaining 20 pups have been exposed to hyperoxia conditions as discussed above. At post-natal day 7, 20 pups (10 hyperoxia and 10 normoxia) receive IT administration of the EV product at a dose of $1\times10^9$ particles, equivalent to $1\times10^{11}$/kg BW. 20 control pups (10 hyperoxia and 10 normoxia) receive a PBS control injection. IT injection is chosen to provide a direct, local administration of the EV product on the site of lung damage, with the final aim to translate this procedure in clinical practice.

The total body distribution is assessed by fluorimetric analysis, thereby evaluating dye concentration in individual organs for each group of 10 pups at different time points (3 and 24 hours) after injection.

Results of this assay show that in pups exposed to normoxic condition, 3 hours post injection, the EV product distributes evenly in the different organs, with a major signal in in the inguinal lymph nodes. 24 hours post injection in normoxic condition the signal can be found in the lymph nodes (inguinal and axillary). In these pups, the labelled EV product is rapidly cleared from the lung and distributed throughout the body. The signal is particularly concentrated in the lymph nodes (inguinal and axillary), which is the only location of retainment at 24 hours.

In pups exposed to hyperoxia, 3 hours after injection the signal in the lungs is completely absent as well as most of the signal in the other organs. Almost all signals can be found in the axillary and inguinal lymph nodes. This can indicate that in hyperoxia conditions there is a faster uptake of the EV product from the site of administration. In hyperoxia treated pups, 24 hours post injection, most of the signal is found in the axillary lymph node (inguinal lymph nodes are devoid of signal).

It should be mentioned that these results are novel, since lymph nodes have never been evaluated as possible target tissues in EVs biodistribution studies. These results clearly show that the lymph nodes are major sites of the EV product accumulation and thus represent fundamental effector sites driving the immunological response to the EV product administration.

Example 12: EVs Activity Using In Vivo Models
of BPD

The experiment is demonstrating the activity of EVs produced according to example 1 in an in vivo model of BPD. Model as described in Porzionato et al. 2018 is used.

Briefly, 30 wild-type Sprague-Dawley rats are used for the study upon approval of the ethic committee. Method of hyperoxia exposure is established by different research team and published in several works (Grisafi et al., 2012, 2013; Marconi et al., 2014; Porzionato et al., 2012 2018). Experiments are performed on rat pups maintained in the chambers with continuous monitoring of oxygen. Experimental animals are exposed to 60% of oxygen for 2 weeks and treated intratracheal with the EV product of the invention. Control animals are exposed to 60% of oxygen for 2 weeks and treated with intratracheal-administered physiological solution (placebo). Normoxia control animals are exposed to 21% of oxygen for 2 weeks and treated intratracheal with the EV product of the invention or physiological solution. EVs are infused at postnatal days 3, 7 and 10.

The efficacy of single or multiple IT injections of the EV product is tested. The dose of the product is $6.4\times10^9$ particles/administration equivalent to a range of $3.19\times10^{11}$ to $5.71\times10^{11}$ particle/kg BW at the three different time points.

Subsequently, lungs of the animals are fixed according to the protocol described by Porzionato et al., 2018 and the lung volume is measured according to the Scherle's method (Scherle, 1970). Histological and immunohistological analysis is performed on lungs slices. Tissue shrinkage factor is estimated following the protocol described by Porzionato et al., 2018. Stereological analysis is performed as described by Porzionato et al., 2018, several parameters are quantified i.e.: i) volume fractions of alveolar air spaces and alveolar septa, ii) total volumes of alveolar air spaces and alveolar septa, iii) surface area density of air spaces, iv) total surface of alveolar air spaces, v) total lung volume, vi) alveolar number and mean alveolar volume among other parameters.

In particular, the efficacy of the IT administration of the EV product is evaluated by morphometric, cytofluorimetric and qRT-PCR analyses to establish the recovery of hyperoxia-induced lung damage and the inflammatory response after the therapy. The morphometric analyses included estimation of lung volume, histological evaluation, immunohistochemical analysis, immunofluorescence analysis of myofibroblast, immunofluorescence analysis of Alveolar type 2 epithelial cells, quantification of samples stained with immunofluorescence technique, alcian blue staining and quantification, protein carbonylation assay, stereological assessment of alveolarization, morphometry of arterial muscle layer, microvessel density, and morphometric analysis of macrophage populations.

All histopathological and morphometric assessments are performed blindly with reference to the experimental groups. All the animals complete the cycle of treatment, including three IT injections of control (vehicle only) or of EV product solutions, respectively on postnatal days 3, 7 and 10.

Postnatal exposure to hyperoxia results in the worsening of all listed histomorphometric parameters, as a result of alveolar destruction. Among these parameters, the decrease of alveolar surface in hyperoxia group is statistically significant. Thickness of septa is also significantly increased, likely due to the inflammatory process (Table 1).

TABLE 1

| | Morphometric parameters of alveolarization | | | | |
| Parameter | Normoxia (N = 10) | Hyperoxia (N = 6) | Hyperoxia + EV-product (N = 9) | F | p |
|---|---|---|---|---|---|
| Lung volume ($cm^3$) | 2.35 ± 0.11 | 1.80 ± 0.23 | 2.29 ± 0.06 | 3.027 | 0.069 |
| $V_{air}$ ($cm^3$) | 1.28 ± 0.65 | 1.00 ± 0.15 | 1.21 ± 0.05 | 2.632 | 0.094 |
| $V_{septa}$ ($cm^3$) | 0.68 ± 0.02 | 0.61 ± 0.05 | 0.73 ± 0.02 | 2.839 | 0.080 |
| Alveolar surface ($m^2$) | 0.130 ± 0.007 | 0.092 ± 0.008 | 0.119 ± 0.003 | 8.138 | 0.002 |
| Mean intercept length (μm) | 39.4 ± 0.99 | 42.8 ± 4.5 | 40.7 ± 1.8 | 0.511 | 0.607 |
| $T_{septa}$ (μm) | 10.5 ± 0.3 | 13.5 ± 0.8 | 12.2 ± 0.4 | 10.33 | 0.001 |

Multiple comparisons (Bonferroni's test) shows that for alveolar surface, hyperoxia group is statistically different both with respect to normoxia and hyperoxia+EV-product, thus EV-product shows a therapeutic effect. For thickness of septa, the hyperoxia group and hyperoxia+EV-product group are not statistically different.

Quantification of cells positive for pulmonary surfactant-associated protein C (SFTPC), that is a specific marker for Lung type II epithelial cells (ATII), performed via immunofluorescence, indicates a marked reduction in ATII after hypoxia-induced damage. Treatment with the EV-product increases the amount of SFPTC in lung tissue. Similar results are obtained by Alcian blue staining, as a marker of glycosaminoglycan production. Moreover, the effect of the EV product on protein carbonylation is tested, which is an established marker of oxidative damage of proteins induced by ROS (reactive oxygen species), generated by the hyperoxia treatment with the resulting inflammatory process. Results show an increased damage in hyperoxic conditions that was reversed by administration of the EV product. No increased mortality is observed in the EV product treated group confirming the safety of the intratracheal administration.

These results show the efficacy of the EV product for use in the treatment of bronchopulmonary dysplasia in a well-established neonatal rat model. Preliminary data suggest that the EV product protects the lung parenchyma from oxidative stress and increases the production of surfactant by AT2 cells, a critical factor in the development of BPD.

Example 13: EVs Activity Using In Vivo Models of Crohn's Disease

The experiment is demonstrating the activity of EVs produced according to example 1 in an in vivo model of Crohn's disease. In short, the experiment is carried out on female 8 week age B57BL/6J mice. Colitis has been induced by administration of 3% sodium dodecyl sulfate (DSS) in drinking water, ad libitum administered over five days. This is a well-established and widely used animal model, being referenced hundreds times by Pub Med (for a review, see Kawada et al., 2007). All the animals are treated according to the appropriate ethical codes. Animals are subdivided in three experimental groups.

Group 1 (n=4, normal controls): intraperitoneal (ip) daily injections of PBS (only vehicle), 0.2 ml from 1 to 5 day;

Group 2 (n=5, colitis induction): like group 1, with addition of 3% DSS in drinking water.

Group 3 (n=4, colitis induction and treatment with EVs): like group 2, with addition of MSC-EVs suspended in 0.2 ml PBS by IP route.

On day 6, the animals are sacrificed using $CO_2$. Colon is excised, and a part of tissue is fixed in formalin for successive histological analysis, whereas another part is immediately frozen in liquid nitrogen and then stored at −80° C. for successive RNA extraction.

Dosage and Administration Route of EVs

EVs are isolated and administered according to the previously described procedure. Administration route: EVs suspended in 0.2 ml of PBS by intraperitoneal way daily administered from 0 to 5 day.

Evaluation of Intestinal Damage

Animal Weight

Disease activity index (faeces evaluation; see Tanaka F, 2008)

Flogosis histopathological signs

Titration of inflammation mediator expression in colon tissue extracts: TNFalfa, IL6, IL-1beta, and Cox2 by RT-PCR.

Statistical Analysis of Results

Data are expressed as mean±SD. Group differences are analyzed by t-test p<0.05 being significant.

Results

In conclusion, the results show that the EVs are suitable to reduce inflammatory reaction of experimental colitis resulting in reduction of disease activity index and amelioration of general conditions. EVs improve the clinical picture and the flogistic response in an animal model of intestinal inflammatory disease.

Example 14: Protocol for Administration and Evaluation of the Safety and Efficacy of the EV Product for Use in the Treatment of BPD in Humans The safety and efficacy of the EV product obtained via the method as described in Example 1 for use in the treatment of BPD, is tested in a human clinical trial. In short, the study is carried on in preterm neonates with high risk of BPD, 23-28 weeks gestational age and birth weight ≤1500 g and being endotracheally intubated receiving mechanical ventilation with fraction of inspired oxygen ($FiO_2$)>25%. The EV product is administered intratracheal. The intratracheal (IT) application of the EV product or saline control solution is not causing an additional risk as only preterm infants receiving invasive ventilation via an endotracheal tube will be eligible.

The study is divided in two phases.

Phase I: Safety and Tolerability of the EV Product

Phase I comprises 18 subjects divided in 6 cohorts of 3 subjects, each receiving one of 3 dose levels of the EV product (Low Dose (LD): $1 \times 10^{10}$ EVs/kg body weight (BW), Medium Dose (MD): $3 \times 10^{10}$ EVs/kg BW, or High Dose (HD): $9\times10^{10}$ EVs/kg BW), and one of two regimens (1 or 3 IT administrations, with 24 h in between multiple administrations).

The main objective is to identify the dose limiting toxicity (DLT) or maximum tolerated dose (MTD) of single or multiple IT administrations of the EV product across 3 different dose levels.

Several aspects are assessed in this phase:

the acute and short-term toxicity of the IT administration of the EV product (single dose or multiple doses at different dose levels) at 36 weeks postmenstrual age (PMA) or at hospital discharge.

DLT within 6 hours and 24 hours after the EV product administration.

AEs (adverse events) and SAEs (serious adverse event) (including case fatalities) reported at different timepoints up to 36 PMA or hospital discharge (related and non-related).

medium-term toxicity of EV product through clinical examination and blood tests (e.g. liver and kidney function tests, haematopoietic indicators, blood pressure, temperature), lung ultrasound, and echocardiography at several timepoints up to hospital discharge.

the number of subjects with oxygen dependence and ventilation support 28 d after birth (Definition BPD according to Jobe A H et al., 2001).

the incidence and severity of BPD after administration of EV product at 36 weeks PMA according to modified NICHD severity grading (Grade I to IIIA) case definition (according to Higgins R D et al., 2018). This will be compared to historical matched cases.

the overall health status after administration of EV product at End Of Study (EOS) (1 yr adjusted age).

mortality at 36 weeks PMA and at EOS (1 yr adjusted age).

Phase IIa: Efficacy of the EV Product in the Treatment of BPD

Phase IIa comprises 70 subjects divided in 2 groups of 35 subjects. One group is treated with the EV product at dose level and regimen selected based on phase I results, and one group with a saline control solution (placebo group).

The main objective is to assess the efficacy of the EV product in the treatment of BPD in a randomized, double blind, placebo-controlled study.

Several aspects are assessed in this phase:

the efficacy of EV product on the incidence and severity of BPD at 36 weeks PMA as compared to a placebo group (saline solution). BPD condition and severity are assessed according to the modified NICHD severity grading (Grade I to IIIA) definition.

the number of subjects with oxygen dependence and ventilation support in both groups 28 d after birth.

the overall health status after administration of the EV product at EOS (1 yr adjusted age) and in placebo group.

mortality at 36 weeks PMA and at EOS (1 yr adjusted age) in both groups.

AEs and SAEs reported at different timepoints up to 36 w PMA or hospital discharge (related and non-related) in both groups.

SAEs reported during the passive surveillance up to EOS (related and non-related) in both groups.

duration of MV/respiratory support, assessment of ROP, NEC, IVH, sepsis up to 36 w PMA or hospital discharge in both groups.

testing of immune markers in tracheal aspirate fluid (IL-6, IL-8, TNFa, TGFb1, IL1b, IL1ra) at several timepoints until the child is intubated.

evaluation of neurodevelopmental condition of infants at 1 yr adjusted age or EOS in both groups.

The present invention is in no way limited to the embodiments described in the examples and/or shown in the FIGURES. On the contrary, methods according to the present invention may be realized in many different ways without departing from the scope of the invention.

The invention claimed is:

1. A process for the manufacturing of a pharmaceutical composition of Extracellular Vesicles (EVs) derived from mesenchymal stromal cells (MSCs), said method comprising:

culturing and expanding MSCs in a serum-free and xeno-free medium comprising human albumin at a concentration between 1 g/l and 5 g/l and human transferrin at a concentration between 55 mg/l and 100 mg/l;

collecting a cell supernatant from said MSCs, wherein said cell supernatant comprises EVs;

filtering said cell supernatant to obtain EVs, wherein said filtering is a two-step filtration process comprising filtering said cell supernatant with a filter having a mesh size of between 1 and 5 μm and bringing a filtrate of the first filtration step over a second filter having a mesh size of below 1 μm; and concentrating a filtrate of the filtering using a tangential flow filtration (TFF) step with a cut-off of 100 kDa.

2. The process according to claim 1, wherein said human albumin and said human transferrin are purified from human plasma or are recombinant albumin and recombinant transferrin.

3. The process according to claim 1, wherein at least $0.25\times10^{9}$ particles/ml medium are produced in a time span of 18 to 24 hours of culturing said MSCs, wherein at least 90% of said particles with particle size of between 0.05 and 0.22 micron are EVs.

4. A pharmaceutical composition comprising Extracellular Vesicles (EVs) derived from mesenchymal stromal cells (MSCs), wherein said composition has at least $1\times10^{11}$ particles per ml, wherein said particles have a particle size between 0.05 and 0.22 micron, and wherein said composition has a human albumin concentration of between 10 and 30 g/l, and wherein at least 90% of said human albumin present in said composition is associated with said EVs.

5. The pharmaceutical composition according claim 4, wherein said composition comprises human transferrin in a concentration of between 60 mg/l to 600 mg/l.

6. The pharmaceutical composition according to claim 4, wherein said composition comprises human transferrin and human albumin at a ratio of between 2 and 60 mg transferrin per g albumin.

7. The pharmaceutical composition according to claim 4 for therapeutic or prophylactic use.

8. The pharmaceutical composition according to claim 4 for use in the prevention or treatment of lung disorders, wherein said lung disorder is an inflammatory lung disease, lung vascular disease, or acute lung injury.

9. The composition for use of claim 3, wherein said inflammatory lung disease is pulmonary hypertension, asthma, bronchopulmonary dysplasia (BPD), allergy, pneumonia, or idiopathic pulmonary fibrosis, and wherein said acute lung injury is associated with sepsis or is acute respiratory distress syndrome (ARDS).

10. The pharmaceutical composition according to claim 4 for use in the treatment of COVID-19 induced or acute pneumonia.

11. The pharmaceutical composition according to claim 4 for use in the prevention or treatment of inflammatory bowel disease.

12. The pharmaceutical composition according to claim 4 wherein said a therapeutically effective amount of said composition is administered to a patient, said patient being an adult, an infant or a neonate, wherein said composition is administered at a dose of $10^9$ EVs/kg to $10^{12}$ EVs/kg of said patient or for each administration.

* * * * *